US005824659A

United States Patent [19]
Strickland et al.

[11] Patent Number: 5,824,659
[45] Date of Patent: Oct. 20, 1998

[54] CYTOPROTECTIVE OLIGOSACCHARIDE FROM ALOE PREVENTING DAMAGE TO THE SKIN IMMUNE SYSTEM BY UV RADIATION

[75] Inventors: Faith M. Strickland; Ronald P. Pelley, both of Galveston; Margaret L. Kripke, Kingwood, all of Tex.

[73] Assignee: Board of Regents, The University of Texas System, Austin, Tex.

[21] Appl. No.: 697,974

[22] Filed: Sep. 4, 1996

[51] Int. Cl.$^6$ .................... A61K 31/715; C08B 37/00; C07G 3/00
[52] U.S. Cl. .................... 514/54; 514/885; 536/123; 536/123.1; 536/124; 536/127; 536/128
[58] Field of Search .................... 514/54, 885; 536/123, 536/123.1, 124, 127, 128; 435/96, 99

[56] References Cited

U.S. PATENT DOCUMENTS

| | | | |
|---|---|---|---|
| 3,103,466 | 9/1963 | Farkas | 167/58 |
| 3,878,197 | 4/1975 | Maret | 260/236.5 |
| 3,892,853 | 7/1975 | Cobble | 424/195 |
| 4,178,372 | 12/1979 | Coats | 424/195 |
| 4,500,510 | 2/1985 | Goldstein | 424/80 |
| 4,585,656 | 4/1986 | Rosenthal et al. | 424/195.1 |
| 4,593,046 | 6/1986 | Gruber | 514/717 |
| 4,627,934 | 12/1986 | Lindauer et al. | 252/552 R |
| 4,670,265 | 6/1987 | Sydiskis et al. | 424/195.1 |
| 4,735,935 | 4/1988 | McAnalley | 514/53 |
| 4,788,007 | 11/1988 | Baron | 252/589 |
| 4,851,224 | 7/1989 | McAnalley | 424/195.1 |
| 4,959,214 | 9/1990 | McAnalley | 424/195.1 |
| 4,966,892 | 10/1990 | McAnalley | 514/54 |
| 5,356,811 | 10/1994 | Coats | 435/267 |
| 5,441,943 | 8/1995 | McAnalley et al. | 514/54 |

OTHER PUBLICATIONS

Wang et al., *Zhiwu Xuebao,* 31(5): 389–392, (1989) ** Abstract Only.

Pelley et al., *Seifen, Oele Fette, Wachse,* 119 (5): 255–268, (1993).

International Search Report dated Jan. 14, 1998 (PCT/US97/17322) (UTFG: 207P).

Strickland et al., "Prevention of ultrviolet radiation–induced suppression of contact and delayed hypersensitivity by *Aloe barbadensis* gel extract," *J. Invest. Dermatol.,* 102(2):197–204, 1994.

Vilkas and Radjabi–Nassab, "The glucomannan system from *Aloe vahombe* (*liliaceae*), III. Comparative studies on the glucomannan components isolated from the leaves," *Biochimie,* 68:1123–1127, 1986.

Wang and Waller, "Current status of quality control of *Aloe barbadensis* extracts," *SÖFW–Journal,* 119:255–268, 1993.

Andersen et al., "Ultraviolet B Dose–Dependent Inflammation in Humans: A Reflectance Spectroscopic and Laser Doppler Flowmetric Study Using Topical Pharmacologic Antagonists on Irradiated Skin," *Photodermatol., Photoimmunol. & Photomed.,* 9:27–23, 1992.

Bergstresser, "Sensitization and Elicitation of Inflammation in Contact Dermatitis," *Immunology Series,* 46:219–245, 1989.

Davis et al., "Processed *Aloe vera* Administered Topically Inhibits Inflammation," *J of the American Podiatric Medical Association,* 79(8):395–397, Aug. 1989.

Gowda, Structural Studies of Polysaccharies from *Aloe saponaria* and *Aloe vanbalenii, Carbohydrate Research,* 83:402–405, 1980.

Gowda et al., Structural Studies of Polysaccharides from *Aloe vera, Carbohydrate Research,* 72:201–205, 1979.

Kripke, "Effects of UV Radiation on Tumor Immunity," *Journal of the National Cancer Institute,* 82(17):1392–1396, Sep. 1990.

Lee, "Our Thanks to Roche Dermatologics, Division of Hoffmann–La Roche Inc." *The Journal of Investigative Dermatology,* 606–610, 1991.

Mandal et al., "Characterization of Polysaccharides of *Aloe Barbadensis* Miller: Part III—Structure of an Acidic Oligosaccharide," *Indian Journal of Chemistry,* 22B:890–893, Sep. 1983.

Mandal and Das, "Structure of the D–Galactan Isolated from *Aloe Barbadenis* Miller," *Carbohydrate Research,* 86:247–257, 1980.

Mandal and Das, "Structure of the Glucomannan Isolated from the Leaves of *Aloe barbadensis* Miller," *Carbohydrate Research,* 87:249–256, 1980.

Paulsen et al., "Structural Studies of the Polysaccharide from *Aloe Plicatilis* Miller," *Carbohydrate Research,* 60:345–351, 1978.

Pelley, "Aloe Polysaccharides and Their Measurement," *Inside Aloe,* Supplement, pp. 1–4, Feb. 1996.

Radjabi et al., "Structural Studies of the Glucomannan from *Aloe vahombe,*" *Carbohydrate Research,* 116:166–170, 1983.

Radjabi–Nassab et al., "Further Studies of the Glucomannan from *Aloe vahombe* (liliaceae). II. Partial Hydrolyses and NMR $^{13}$C Studies," *Chimie,* 66:563–567, 1984.

(List continued on next page.)

*Primary Examiner*—John Kight
*Assistant Examiner*—Howard C. Lee
*Attorney, Agent, or Firm*—Arnold, White & Durkee

[57] ABSTRACT

The present invention relates to a glucose-rich, mannose-containing oligosaccharide described herein has a molecular weight of approximately 1,000–5,000 daltons and is separated from interfering aloe components. The oligosaccharide inhibits loss of skin immunocompetency which is induced by ultraviolet irradiation. The oligosaccharide is obtained by cellulase cleavage of a precursor block polysaccharide of Aloe (FIG. 1) and has about 75% glucose, about 25% mannose and trace galactose. The precursor polysaccharide has a molecular weight of >2,000,000 daltons, is about 73% hexose with a total hexose to reducing sugar ratio of about 23:1. This polysaccharide is about 7% glucose, about 85% mannose and about 4% galactose. Also described is a method for obtaining an immunoprotective oligosaccharide by treating an Aloe extract with cellulase at a concentration of less than about 2 grams per 215 liters.

6 Claims, 12 Drawing Sheets

OTHER PUBLICATIONS

Reeve et al., "Differential Protection by Two Sunscreens from UV Radiation–Induced Immunosuppression," *The Journal of Investigative Dermatology,* 97(4):624–628, Oct. 1991.

Reeve et al., "The Protective Effect of Indomethacin on Photocarcinogenesis in Hairless Mice," *Cancer Letters,* 95:213–219, 1995.

Roboz and Haagen–Smit, "A Mucilage from *Aloe vera,* " *Journal of the Am Chem. Soc.,* 70:3248–3249, Oct. 1948.

Solar et al., "Mise En Evidence Et Etude Des Proprietes Immunostimulantes D'Un Extrait Isole Et Partiellement Purifie A Partir D'Aloe Vahombe," *Arch Inst Pasteur Madagascar,* 47:9–39, 1979.

van Praag et al., "Effect of Topical Sunscreens on the UV–Radiation–Induced Suppression of the Alloactivating Capacity in Human Skin In Vivo," *The Journal of Investigative Dermatology,* 97(4):629–633, Oct. 1991.

Vermeer et al., "Effects of Ultraviolet B Light on Cutaneous Immune Responses of Humans with Deeply Pigmented Skin," *The Journal of Investigative Dermatology,* 97(4):729–734, Oct. 1991.

Wolf et al., "Analysis of the Protective Effect of Different Sunscreens on Ultraviolet Radiation–Induced Local and Systematic Suppression of Contact Hypersensitivity and Inflammatory Responses in Mice," *The Journal of Investigative Dermatology,* 100(3):254–259, Mar. 1993.

Womble and Helderman, "Enhancement of Allo–Responsiveness of Human Lymphocytes by Acemannan (Carrisyn™)," *Int. J. Immunopharmac.,* 10(8):967–974, 1988.

Yagi et al., "Aloe Mannan, Polysaccharide, From Aloe Arborescens Var. Natalensis," *Planta Medica,* 31:17–20, 1977.

Yagi, et al., "Structure Determination of Polysaccharides in *Aloe arborescens* Var. Natalensis," *Planta Medica,* 213–219, 1986.

Yagi et al., "Structure Determination of Polysaccharides in *Aloe saponaria* (Hill.) Haw. (Liliaceae)," *Journal of Pharmaceutical Sciences,* 73(1):62–65, Jan. 1984.

*High moisture content (even after two days of lyophilization) requires that caution be employed in interpreting gravimetric result.

CYTOPROTECTIVE OLIGOSACCHARIDE FROM ALOE PREVENTING DAMAGE TO THE SKIN IMMUNE SYSTEM BY UV RADIATION

The present invention relates generally to protection of the immune system. More particularly, it concerns preventing or correcting immunological damage to skin exposed to ultraviolet irradiation.

Aloe extracts have long been known to be therapeutically useful and to contain medically beneficial ingredients. The present invention involves a novel factor of aloe extracts useful to protect the skin immune system subsequent to shortwave ultraviolet irradiation injury. A process is described herein for the separation, isolation and use of biologically active materials from aloe e.g., *Aloe barbadensis*. The separation of this factor from other aloe extract components, its description and use are important aspects of the present invention.

BACKGROUND OF THE INVENTION

Ultraviolet Light and the Skin Immune System

Recent reports directed to the global depletion of ozone in the atmosphere, including the discovery of the Antarctic "hole" in the ozone layer, have focused interest in the effects of ultraviolet radiation on human health. Although some exposure to ultraviolet radiation is needed for humans to produce vitamin D, the evidence overwhelmingly shows that ultraviolet radiation exposure is related to a range of health problems. Specifically, it is well known that ultraviolet exposure causes sunburn and is involved in the induction of certain skin cancers.

In addition to these established health concerns, research has provided recent evidence suggesting that exposure to ultraviolet radiation may have detrimental effects upon a variety of immunological reactions and may decrease the immune system's ability to respond to various infectious agents. See, e.g. Kripke, *Journal of the National Cancer Institute*, 1,392–1,396 (1990). In particular, it is thought that ultraviolet radiation-induced injury to the skin immune system supplies a second factor necessary for the development of common skin cancers. The primary factor in the induction of skin cancer is the mutational damage done by ultraviolet radiation to the DNA of the generative cells in the skin. However these early malignant cells are thought to be eliminated by the normal functioning of the skin immune system. When the immune function of the cells in the skin is suppressed by ultraviolet radiation, the cells cannot perform their usual surveillance function and eliminate very early skin cancers.

Related References in the Scientific Literature
Treatment of Irritation and Inflammation versus Prevention of Suppression of the Skin Immune System The effect of ultraviolet radiation in suppressing the skin immune system is separate and dissociable from the grossly apparent inflammatory and irritant effects of ultraviolet radiation on the skin such as erythema (redness) edema (swelling) and flaking or scaling (hyperkeratosis). Modalities taught in the prior art for the prevention and treatment of skin inflammation and irritation do not appear to be of utility in the treatment of ultraviolet-light-induced suppression of the skin immune system. For example, Reeve et al., *J. Invest. Dermatol.*, 97:624–628 (1991) reported that topical application of certain ultraviolet radiation-absorbing compounds, such as certain sunscreens, were effective in preventing ultraviolet radiation-induced erythema and edema but that some of these sunscreens failed to prevent immunosuppression in a mouse model as measured either by contact hypersensitivity or by induction of susceptibility to transplanted tumor cells. Thus prevention of irritation and inflammation did not prevent suppression of the skin immune system. This was confirmed by Von Praag et al., *J. Invest. Dermatol.* 97:629–633 (1991) and Wolf et al., *J. Invest. Dermatol.* 100:254–259 (1994) who reported that commercial sunscreens may not fully protect against ultraviolet radiation-induced immunological alterations. Indirect evidence for this idea was presented by Vermeer et al., *J. Invest. Dermatol.* 729–734 (1991) by studing the immune reaction of human subjects to the contact allergen dinitrochlorobenzene. They concluded that the pigmentation levels (of either dark skinned or tanned subjects) did not appear to protect the skin immune system from the damaging effects of ultraviolet radiation (although it is well accepted that skin pigmentation protects the skin against the irritant and inflammatory effects of ultraviolet radiation).

These studies suggest that while sunscreens alone do prevent inflammation and irritation they do not provide complete prophylactic protection against the immunosuppressive effects of ultraviolet radiation. Furthermore, pharmacologic agents which are commonly and traditionally employed for the treatment of irritated and inflamed skin are without effect in treating the suppression of the skin immune system induced by exposure to ultraviolet radiation when they are applied after the injury is manifest. Andersen et al., *Photodermatol., Photoimmunol. & Photomed.* 9:17–23 (1992), examined in humans the effect of treatment with the four commonest anti-inflammatory agents of ultraviolet radiation-injured skin upon edema and erythema. Topically applied corticosteroids were most effective in reducing inflammation and irritation followed respectively by indomethicin, acetylsalicylic acid (aspirin), and diphenhydramine (Benedryl®). Aspirin and Benedryl®have not been demonstrated to be capable of restoring the ultraviolet radiation-induced damage to the skin immune system. Local application of corticosteroids reduce the skin immune response as taught by Bergstresser, *Immunology Series*, 46:219–245 (1989), and many others. Although indomethacin has been demonstrated by Reeve et al., *Cancer Letters*, 95:213–219 (1995), to inhibit photocarcinogenesis this effect appears to involve both the initiation period and the promotion period of tumor development and thus is thought to be a function of a generalized anti-carcino-genesis effect rather than an effect on the skin immune system. Thus there appears to be a pattern whereby agents capable of suppressing inflammation and irritancy do not protect the skin immune system. Recognizing this dissociation of the phenomenon of inflammation/irritation from the induction of skin cancer, academic experimental dermatologists have virtually abandoned the use of erythema and edema as endpoints for the deleterious effects of ultraviolet radiation in the induction of skin cancer and have instead adopted direct measures of carcinogenesis (mutational changes in the DNA of skin cells and direct measurement of the function of the skin immune system).

Aloe and Treatment of the Skin

Anti-Inflammatory and anti-irritant activities have been taught to be inherent to Aloe materials by many patents and publications. The first of these was by Farkas (U.S. Pat. No. 3,103,466, Sep. 10, 1963) who disclosed the use of Aloe Vera to provide analgesic effect upon inflammed or irritated skin. The following section summarize patents which teach the use of unfractionated or fractionated "Aloe Vera" (*Aloe barbadensis* Miller) extracts for relief of inflammation and irritation. These inventors fail to disclose an understanding of the difference between treatment of inflammation and irritation versus restoration of the skin immune response. The first reflection of this are such patents that view Aloe preparations as having utility only as sunscreens (e.g. Baron, U.S. Pat. No. 4,788,007) and thus having utility only for prevention and not for treatment. Those inventors which appreciate the utility of Aloe preparations for therapeutic purposes in their claims envision only effects that can be seen (erythema and swelling) or perceived (itching and pain). For example, those patents which directly claim relief of pain and itching (Rosenthal, U.S. Pat. No. 4,585,656 and Gruber, U.S. Pat. No. 4,593,046) offer embodiments that result in products ineffective in restoring the skin immune system (infra vide Examples). Those patents concerned with processing (Maret, U.S. Pat. No. 3,878,197; Cobble, U.S. Pat. No. 3,892,853 and Coats, U.S. Pat. No. 4,178,372) which do not claim biological activity but refer to biological activity in examples teach little to one skilled in the art. Their examples are so vague with regard to biological activity on topical application that one would not be led to understand the difference between the treatment of inflammation and irritantcy versus restoration of the skin immune system. Therefore it is not surprising that commercial Aloe products are ineffective in prevention suppression of the skin immune response by ultraviolet radiation.

Different Assays of Biological Effect Lead to Identification of Different Therapeutic Modalities Those skilled in the art can only develop and produce products with the efficacy inherent in a disclosed invention. Such is the case for anti-inflammatory activity (e.g. Davis et al., "Processed Aloe vera administered topically inhibits inflammation", *J. Amer. Podiatric Med. Assoc.* 79:395–397 (1987)). Applications of different mechanism, mediated by different molecules, will be non-inherent and non-obvious. Thus, others with claims for biological activity view the function of topically applied Aloe preparations as the promotion of wound healing (e.g. Goldstein, U.S. Pat. No. 4,500,510 and McAnalley, U.S. Pat. No. 4,966,892). This has led to the selection of the fibroblast in the in vitro test system for biological activity (e.g. McAnalley, U.S. Pat. No. 4,966,892, Examples 7, 11, and 25) a cell system with no role in the immune response. Thereby guided, the inventor claimed to have identified polysaccharide as the only active molecule in Aloe (e.g. McAnalley, U.S. Pat. No. 4,735,935 and others following). As described in certain embodiments of the present invention, immune cells and indirectly keratinocytes are involved in the ultraviolet light/skin immune response system. Also described herein is the identification of families of compounds differing from those previously disclosed (polysaccharides, McAnnaley; anthraquinones, Skydiskis, U.S. Pat. No. 4,670,265 & Baron, U.S. Pat. No. 4,788,007). Those properties truly inherent in an invention will lead one skilled in the art only to established therapeutic molecules rather than to novel molecules.

Essentially, all Aloe-containing cosmetics sold over the counter in the domestic market employ Aloe preparations treated with activated charcoal in order to prevent color change with time. The Aloe-absorbed activated charcoal is discarded as an industrial waste product. The technologies of Maret (U.S. Pat. No. 3,878,197), Cobble (U.S. Pat. No. 3,892,853), Coats (U.S. Pat. No. 4,178,372) and Lindauer et al. (U.S. Pat. No. 4,627,934) which function primarily by inhibiting bacterial growth are ignored by industry as non-utilitarian because they do not efficiently prevent color change. Davis et al. (e.g. "Processed Aloe vera administered topically inhibits inflammation", *J. Amer. Podiatric Med. Assoc.* 79:395–397 (1987)) teaches that absorption of Aloe with activated charcoal removes anti-inflammatory activity. We have found that the anti-inflammatory in Aloe can be eluted from the Aloe-absorbed activated charcoal industrial waste product and that it has a novel structure previously undescribed—that of a Cinnamoyl-C-Glycoside Chromone. In the parallel application for Letters Patent we demonstrate a second factor in Aloe absorbed to activated charcoal. This factor is chemically distinct from the Cinnamoyl-C-Glycoside Chromone. We further demonstrate therein that a portion of the therapeutic activity for restoration of the skin immune system subsequent to damage by ultraviolet radiation is associated with that compound. This separates the functionality of anti-inflammation and anti-irritancy from that of treatment of the skin immune system and thereby establishes that the functionality we teach herein is noninherent and nonobvious from that which is taught previously and from that which led to the isolation of the Cinnamoyl-C-Glycoside Chromone. Herein we further exploit this principle and thereby develope a further novel molecule. This molecule is an oligosaccharide, cleavable by cellulase from the native polysaccharide of Aloe, which is also capable of preventing ultraviolet radiation induced suppression of the skin immune system—albeit by a mechanism different than that of the Activated Charcoal Absorbable factor disclosed in the parallel application. This oligosaccharide compound is chemically distinct and readily seperable from the previous polysaccharides described for the various species of Aloe.

Aloe Polysaccharides in the Scientific Literature

In general, the dominant polysaccharide of *Aloe barbadensis* (*Aloe vera* Linnaeus, archaic; also variously and incorrectly *Aloe Vera* etc.) is the glucomannan classically described for *Aloe Vera* (sic) by Roboz and Haagen-Smit ("A Mucilage from *Aloe Vera*." *J. Am. Chem. Soc.* 70:3248–3249, 1948). The structure of this major polysaccharide, purified by alcohol precipitation and dialysis, was first elucidated by Gowda et al. ("Structural studies of polysaccharides from *Aloe vera*." *Carb. Res.* 72:201–205, 1979.) from *Aloe vera* (sic). These investigators further fractionated the precipitated polysaccharides based on a gradient of alcohol concentrations. They found a glucose to mannose ratio of 1:4.5 in the more lightly acetylated (9.25% m/m) less alcohol soluble fraction. The more highly alcohol soluble fractions had a somewhat higher mannose content (glucose:mannose 1:13.5 to 1:19) and were somewhat more heavily acetylated (10.3 to 17.2% m/m). In all cases a molecular weight of >200,000 was assigned based on total exclusion from G-200 chromatography gel. Mandal and Das ("Structure of the glucomannan isolated from the leaves of *Aloe barbadensis* Miller." *Carb. Res.* 87:249–256, 1980.) have also studied the glucomannan of *A. barbadensis*. Analysis of the polysaccharide purified by alcohol precipitation followed by precipitation with Fehling solution yielded a glucose to mannose ratio of 1:20.6 and suggested a repeating subunit of 3,276 daltons. The average molecular weight determined by osmometry was 15,000 daltons. This group also purified and characterized two other polysaccharides from *A. barbadensis*, one of which is a galactan ("Structure of the D-galactan isolated from *Aloe barbadensis* Miller." *Carb. Res.* 86:247–257, 1980.) and the other of which is a pectin (Mandal, Gosh and Das, "Characterization of polysaccharides of *Aloe barbadensis* Miller: Part III—Structure of an acidic oligosaccharide." *Ind. J. Chem.* 22B:890–893).

Polysaccharides have also been purified from other Aloe species (*arborescens, plicatilis, vahombe* and *saponaria*). The first of these to be characterized (in fact the first Aloe polysaccharide to be subjected to detailed examination) was the mannan of *A. arborescens* (Yagi et al., "Aloe mannan, polysaccharide, from *Aloe arborescens* var. *natalensis."* *Planta Medica* 31:17–20, 1977.). These investigators dialysed the gel, precipitated protein with chloroform and isolated the polysaccharide by repeated cycles of precipitation with acetone. Analysis of the isolated polysaccharide by hydrolysis and paper chromatography revealed mannose to be the predominant sugar. Spectroscopy suggested that the sugars were b linked and saponification revealed that the mannan was acetylated. The molecular weight, determined by ultracentrifugation was 15,000 daltons. Lastly, these investigators were the first to determine a biological activity for an Aloe polysaccharide. Ten injections of either 5 or 100 mg of Aloe mannan produced a 38 to 48% reduction in the growth rate of Sarcoma 180—a classical assay for stimulation of immune responses to tumors.

Paulsen et al. ("Structural studies of the polysaccharides from *Aloe plicatilis* Miller." *Carb. Res.* 60:345–351, 1978) reported the isolation of a glucomannan from *A. plicatilis* gel by dialysis. This polysaccharide had a glucose: mannose ratio of 1:2.8 and a molecular weight by gel filtration upon Sepharose 4B of at least 1,200,000 daltons. Reducing sugar analysis indicated that the polysaccharide was essentially linear and almost all sugars bore at least one acetyl group.

The polysaccharides of *Aloe saponaria* and *A. vanbalenii* were isolated by alcohol precipitation and dialysis and preliminary characterization performed by Gowda ("Structural studies of polysaccharides from *Aloe saponaria* and *Aloe vanbalenii."* *Carb. Res.* 83:402—405, 1980). The predominant polysaccharide of *A. saponaria* is a linear mannan with negligible amounts of glucose and a 20.7% (m/m) degree of acetylation. The predominant polysaccharide of *A. vanbalenii* is also a pure mannan with significant (19.5% m/m) acetylation. Neither molecular weight nor biological activity were reported.

*Aloe vahombe* has been described as having immunoadjuvant activity (Solar et al., *Arch. Inst. Pasteur Madagascar.* 47:1–31, 1979). Radjabi et al. ("Structural studies of the glucomannan from *Aloe vahombe."* *Carb. Res.* 116: 166–170, 1983) isolated the polysaccharide by ethanol precipitation and gel filtration using Sephadex G-100. The 1–4 linked polysaccharide, which eluted in the Vo upon gel filtration (molecular weight≧had a glucose to mannose ratio of 1:2.6 and 33% of the glucose residues were acetylated. In these respects, this polysaccharide more closely resembles that found in *A. plicatilis* than it does *A. barbadensis*. Further studies of the *A. vahombe* polysaccharide by Radjabi-Nassab et al. ("Further studies of the glucomannan from *Aloe vahombe* (liliaceae). II. Partial hydrolyses and NMR $^{13}$C studies." *Biochimie* 66:563—567, 1984) confirmed that the basic 1–4 linkage was of the b configuration and that cellulobiose-like units were rare.

More recently, Yagi's laboratory published ("Structure determination of polysaccharides in *Aloe saponaria* (Hill.) Haw. (Liliaceae)." *J. Pharmaceutical Sci.* 73: 62–65, 1984) investigations on 2 mannans from *A. saponaria* isolated by dialysis of gel, size exclusion chromatography and ion exchange chromatography (which removed charged materials. *Aloe saponaria* (As) mannan-1, isolated from material harvested in September 1980 consisted of a linear 1–4 linked, acetylated (18% m/m) polysaccharide composed exclusively of mannose residues. Molecular weight based on gel permeation chromatography was 15,000 daltons. *A. saponaria* mannan2, isolated from material harvested in December 1980 was similar to mannan-1 excepting that its molecular weight was 66,000, a "trace" amount of glucose was present, the degree of acetylation was lower (10% m/m), and branching was evident. Biological activity of mannan-1 after parenteral administration was evidenced by inhibition of Carrageenin-induced edema. In a 1986 publication (received by the journal 9 December, 1985) Yagi's group re-examined the polysaccharides of *A. dialysis*. Neutral polysaccharide was isolated by dialysis, removal of charged materials by chromatography on DEAE cellulofine and gel permeation on Sepharose 6B. Three polysaccharides were observed which differed in their molecular weight and structure. Some confusion exists in this publication because the positions at which polysaccharides A, B and C elute from the preparative gel filtration column (A largest, B midsized and C smallest) do not correspond to the molecular weights described for the polysaccharides in the text (A, MW 15,000; B, 30,000; and C, 40,000). Assuming that the assignments in the text are correct (and that FIG. 2 is mislabelled) the conclusions are as follows. Polysaccharide A (MW 15,000) is present in the largest quantity and it is dextran-like (1,6 linked glucose). Polysaccharide C (MW 40,000) is present in second largest amounts and it is an acetylated (10% m/m) mannan of b1-4 linkage. Present in trace amounts was an arabinogalactan (Polysaccharide B) of intermediate (30,000) molecular weight. Polysaccharide C (which corresponds to the polysaccharide this group described in 1977 with the exception of molecular weight— 15,000 in 1977 and 40,000 in 1986) was biologically active in that it enhanced phagocytosis and promoted the reduction of NBT dye by human leukocytes. This finding suggests a link between the anti-tumor effect described in 1977 (generally thought to be immune mediated) and activation of the phagocytic arm of the immune response.

Summarizing the published scientific literature, prior to 1986 on the structure and biological activity of Aloe polysaccharides one may come to the following conclusions. They are predominantly linear polymers of mannose linked to mannose by a beta (b) 1-4 linkage. In some cases they contain a significant amount of glucose. There appear to be two forms described. One is a highly linear mannose rich form of molecular weight 15,000 daltons. The other is of higher molecular weight, which weight could not be determined because of the limitations of the technology available. These polysaccharides are immunostimulants and appear to act by activation of phagocytic cells.

Aloe Polysaccharides in the Patent Literature

This invention consists of a novel oligosaccharide cleaved from the native predominant Aloe polysaccharide. Since the correct structure of the precursor polysaccharide is crucial to teaching the process by which the cleaved oligosaccharide is produced, a background of the Aloe polysaccharides is in order.

Previous Patents disclosing the structure, process of obtaining, and utility of Aloe polysaccharides are relatively few compared to the literature just reviewed. McAnalley (infra vide) has received three Letters Patent that disclose the structure of Aloe mannan and a process (alcohol precipitation) for isolating it. Coats in U.S. Pat. No. 5,356, 811 describes a method for destroying (Claim 1b) the Aloe polysaccharide in order to boost the yields of juice obtained thereby. Finally, Davis (U.S. Pat. No. 5,487,899) teaches that it is important to include the slimy coat of the gel fillet together with the homogenized gel fillet if the full utility of Aloe gel is to be obtained for use as a wound bandage. Although the Davis patent employs polysaccharide the correct structure of which we teach, the field of Davis' invention is radically different. Similarly, although we teach the correct structure of the molecule that Coats' seeks to be rid of, the process we employ is antithetical to his. The disclosures of McAnalley are closest to the field of this invention and it is necessary to understand how his structure was incorrect and why knowledge of the correct structure leads to a novel process to make a compound (oligosaccharide) that he discards.

Acemannan Structure and Molecular Weight by Process

Numerous Letters Patent have been issued, beginning in 1988 to McAnalley concerning *A. barbadensis* mannans which are variously termed Acemannan, Carrisyn® or CARN 750®. He claims, in U.S. Pat. No. 4,735,935 (Apr. 5, 1988), all acetylated b1-4 mannans from the disaccharide (degree of polymerization n=2) to the high linear polymers (n=50,000) and states that the polymer is at least 80% mannose. In the examples in the various patents the molecular weights of the various materials exemplified varies greatly. By way of process, in the '935, patent, Example 1 (columns 20–21) specifies that the product is produced by ultrafiltration removing undesirable compounds of less than 10,000 MW (nominal) and retaining the polysaccharide (presumably of nominal molecular weight >10,000). It is further specified that this retained fraction can be further fractionated by passage through an ultrafilter of nominal molecular weight cutoff 50,000 wherein a ultrafiltrate is obtained of desired material.

Analysis of Acemannan Molecular Weight

Example 27 of the '935 patent illustrates analytical molecular weight as determined by high pressure liquid chromatography using a 7.5×300 mm Beckman spherogel TSK 2000 column. Detection of eluted material was by nonspecific methods. Unfortunately, the chromatogram, which is crucial to evaluating the data, is not exemplified. From the tabulation of calibration it is apparent that analytical precision is obtained only in the molecular weight range of 40,000 to 9,000 daltons. Three classes of materials were exemplified with molecular weights of >80,000, ≧10,000 and <1,000 daltons. From the summary (65, lines 28–30; "cleave the function groups and glycosidic bonds (b(1-4)) thus reducing or eliminating its activity.") and Claim 1a ("substantially non-degradable") it is apparent that materials in the the third chromatographic region are undesirable. By reference to the published scientific literature reviewed above, it is highly probable that the first described materials (50, line 59 "Fraction #1, MW>80,000") corresponds to the material described by Gowda et al. ("Structural studies of polysaccharides from *Aloe vera.*" Carb. Res. 72:201–205, 1979) and that the second material (line 60, MW≧10,000) corresponds to the material of molecular weight 15,000 daltons described by Mandal and Das ("Structure of the glucomannan isolated from the leaves of *Aloe barbadensis* Miller." Carb. Res. 87:249–256, 1980). The third material consists of undesired material of molecular weight less than 10,000 daltons. This material is removed by dialysis or solvent precipitation by investigations previously published by others in the scientific literature.

With all of these assumptions in mind, the exemplification taught by McAnalley can be understood as follows. There are two polysaccharides in Acemannan. One of molecular weight greater than 80,000 daltons which actual molecular weight cannot be more precisely determined because it is beyond the analytical range of the method. There is a second polysaccharide of molecular weight of perhaps 12,000 daltons. There is a third region of undesired contaminants and breakdown products. The content in Acemannan of these materials varied greatly in Example 27 as is seen in the summary below.

| | Percentage of Material in Class (Range) | | |
|---|---|---|---|
| | Fraction #1 (>80,000 d) | Fraction #2 (>10,000 d) | Fraction #3 (undesired) |
| Experimental Preparations n = 6 | 47% (12–60%) | 18% (15–21%) | 35% (24–67%) |
| Manufacturing Preparations n = 2 | 28% (19–37%) | 15% (7–24%) | 57% (56–57%) |

Based on the disclosures taught by McAnalley this implies that the process exemplified is relatively uncontrolled in its enzymatic breakdown.

The inventor then infers later in Example 27 and in Examples 31 and 32 that the process of monitoring the breakdown of Acemannan can be achieved by IR spectroscopy. This is exemplified in its utility in preventing breakdown (and by inference production of the undesired Fraction 3 materials of Molecular Weight <10,000 daltons). The method of processing taught is to store and transport the leaves at reduced temperature and process leaves quickly, a process employed by almost all companies in the field and one exemplified and claimed in the patents cited herein.

Example 5 of U.S. Pat. No. 4,851,224 to McAnalley is concerned with, among other things, the isolation, purification and characterization of the Carrisyn® Acemannan polysaccharide. The '224 Patent exemplifies further determination of molecular weight and composition of matter. Therein, (30, lines 60–63) it is explicitly stated that "is generally contaminated with proteins, monosugars, oligosaccharides and inorganic salts. These contaminants do not affect the bioactivity of the product" (Emphasis added). The Acemannan polysaccharide is further (31, lines 2–3) described as a (non-filterable product which is mainly acetylated polymannose "with molecular weight by dialysis of greater than" 12,000–14,000 (line 14). High pressure size exclusion chromatography using TSK 5000 column and a refractometric (nonspecific) detector was used to further characterize this material as to molecular weight. Interpretation of the data exemplified is complicated because the figures as illustrated do not correspond to the data referred to in the test. The FIG. 12 referred to in the text (calibration profile) is assumed to be the drawing illustrated as FIG. 11. Similarly, the FIG. 13 referred to in the text exemplifing an analytical profile is assumed to be the drawing illustrated as FIG. 12. Lastly it is assumed that the flow chart referred to as FIG. 11 in the text is the same as the flow chart drawing illustrated as FIG. 13. With these assumptions in mind, the data can be interpreteted as being consistent with the Acemannan product consisting of a Material "A" of molecular weight >100,000 and a Material "B" having a molecular weight "greater than 10,000 but less than 100,000 daltons". Inspection of the figures, in fact, suggest a molecular weight of approximately 12,000 for Material "B". It is further stated that "The sum of peaks A and B constitute the active fractions" although the nature of the activity is unspecified and unexemplified. This data, taken together with the Summary (42, lines 21–31) indicates that "A" (>100,000 daltons) is active and upon decomposition converts to "B" (~12,000 daltons) and subsequently to inactive "C" (dialysable, alcohol-soluble, MW less than 10,000).

Chemical Composition of Acemannan

The '935 patent addresses the issue of the importance of the sugar composition of Acemannan in Example 13 and concludes (38, lines 30–31) that by hydrolysis "Carrisyn® is essentially mannose. Example 12 (columns 36–37) makes the point by way of the parison with the glucomannan from the Konjac plant that glucose is unimportant.

Example 5 of the '224 Patent is also concerned with the chemical composition of the claimed biologically active, Carrisyn® Acemannan product and in particular with the predominance of mannose in the polysaccharide. They state (31, lines 16–17) that adulteration with inactive, non-claimed materials "could be detected by a high galactose or glucose to mannose ratio". Furthermore, (34, lines 3–5) "On the basis of infrared spectroscopy alone, Carrisyn® extract is a polysaccharide of essentially b mannan-linked D-mannose with O-acetyl group side chains." Noting the structure determined by acid hydrolysis followed by HPLC (36,lines 22–25) "It is noted that mannose is the major component of the polymer signifying that the polysaccharide is essentially composed of mannose sugar units". With reference to analysis by gas chromatography (37, lines 36–37) it is stated "Carrisyn® extract is essentially a polymannose polysaccharide". Lastly for GC/MS analysis, (39, lines 38–39) "it is deduced that Carrisyn® extract is mainly a(1-4) linked linear polymer of mannose.

The final probe of the chemical structure of Acemannan as envisioned by McAnalley is found in studies of enzymatic degredation. Throughout all sections of all patents, McAnalley stresses that the biological activity of Acemannan is very sensitive to degradation by glycosidases. As referred to above in the section on molecular weights, production of cleavage fragments of molecular weight less than 12,000 daltons is stressed as being associated with loss of activity although this claim is unexemplified by data. Example 12 of the '935 patent uses a commercial preparation of cellulase to degrade Acemannan in order to obtain monosaccharide mannose for analysis.

In contrast to the deleterious action of cellulase, U.S. Pat. No. 4,959,224 to McAnalley exemplifies that treatment with protease is without noticable effect. In Example 5 protease treatment is used to aid in the removal of contaminating proteins (30 line 60 to 31 line 7).

Chemical Modification of Acemannan

McAnalley in U.S. Pat. No. 4,959,214 claims (#8–15) and exemplifies (Example 38) numerous chemical modifications of Acemannan polysaccharides. These modifications include oxidation (with hydrogen peroxide), periodate treatment, phosphorylation, methylation, carboxylmethylation, sulfation and crosslinking (with epichlorhydrin or formalin). However, no mention is made of enzymatic processing with cellulase to yield a cleavage product, particularly one chemically distinct from Acemannan.

Summary of Polysaccharide Structure

There appears to be a consensus between the publications in the scientific literature, reviewed above, and the Patents reviewed above, concerning the structure of Aloe polysaccharides. There exists in Aloe an essentially linear, acetylated polysaccharide of discrete molecular weight between 12,000 and 15,000 daltons. In the case of A. arborescens (Yagi et al., 1977), barbadensis (Mandal & Das, 1980) and saponaria (Yagi et al., 1984) it has the following structure:

Structure A (2,3 Acetyl Man, β 1-4 6 Acetyl Man)$_{38}$

This is the structure later claimed by McAnalley (1988). There also exists a higher homopolymer of this linked together through 1,6 linkages:

Structure B [(2,3 Acetyl Man, β 1-4 6 Acetyl Man)$_{38}]_n$ where n is at least 8 and probably generally much larger. This structure has been reported for A. barbadensis (Gowda, 1979), saponaria (Yagi et al., 1984) and arborescens (Yagi et al., 1986). This structure has also been claimed by McAnalley (1988). Mannans of chemical composition similar to the above have also been described for A. saponaria and vanbalenii (Gowda, 1980) although it was unstated whether they were present as Structure A or Structure B. Glucomannans have been described for A. plicatilis (Paulsen et al., 1978) and vahombe (Radjabi et al., 1983) similar to Structure B excepting that glucose substitutes for some of the mannose residues.

Biological activity for suppressing inflammation and increasing the immune response has been claimed for both structures by Yagi et al. (1977, 1984 and 1985) by mechanism of activating phagocytic cells and for increasing the rate of wound healing (McAnalley, 1988) by mechanism of increasing the growth of fibroblasts.

United States Patents differ greatly in the methods disclosed for processing Aloe with regard to polysaccharides. McAnalley (1988 and following) teaches the absolute need to prevent the breakdown of Structure B to Structure A. Coats (1995) teaches the opposite claiming a method of process that breaks down all Structure A and B.

The Problem to Which the Invention Is Addressed

The production of extracts of Aloe leaves that consistently exhibit the ability to prevent Ultraviolet B radiation-induced injury to the cutaneous immune system has not been achieved. Furthermore, commercial materials consisting of Structure A shown above are not active for this use. Therefore, there is a need to know the structure of the active component in order to manufacture it more consistently and stabilize its activity. It is possible that the Structure B above is incorrect. Determination of the correct structure and the development of processes that correctly produce the active component from Structure B will teach the correct way of producing and stabilizing the active product.

We teach that Structure A shown above is a correct structure but that it is not the active compound for our desired utility (although we also verify that it has the utility that McAnalley claims). We teach the correct structure for B and teach a process for obtaining a novel, non-Acemannan oligosaccharide of novel utility.

SUMMARY OF THE INVENTION

A glucose-rich, mannose-containing oligosaccharide described herein has a molecular weight of approximately 1,000–5,000 daltons and is separated from interfering aloe components. The oligosaccharide inhibits loss of skin immunocompetency which is induced by ultraviolet irradiation. The oligosaccharide is obtained by cellulase cleavage of a precursor block polysaccharide of Aloe (FIG. 1) and has about 75% glucose, about 25% mannose and trace galactose. The precursor polysaccharide has a molecular weight of >2,000,000 daltons, is about 73% hexose with a total hexose to reducing sugar ratio of about 23:1. This polysaccharide is about 7% glucose, about 85% mannose and about 4% galactose. Also described is a method for obtaining an immunoprotective oligosaccharide by treating an Aloe extract with cellulase at a concentration of less than about 2 grams per 215 liters (FIG. 2).

The glucose-rich mannose-containing oligosaccharide of the present invention having a molecular weight of approximately 1,000–5,000 Daltons is characterized as being separated from interfering Aloe components and inhibiting of skin immunocompetency induced by ultraviolet irradiation. Therapeutic compositions for the alleviation of UV-induced immune system damage is readily preferable utilizing the oligosaccharide of the present invention in any of the well known pharmaceutically acceptable excipients usable for application to the skin.

Another method for inhibiting immunosuppression induced by ultraviolet irradiation is described wherein a glucose-rich and mannose-containing oligosaccharide is extracted from an aloe extract which has a molecular weight of about 1,000–5,000 and is topically administered to an animal subjected to ultraviolet irradiation.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

$$\text{Relative Viscosity} = \frac{\text{Time of Flow Experimental} - \text{Time of Flow of Water}}{\text{Time of Flow, O Time of Flow of Water}} \times 100$$

FIG. 8 effect of cellulase treatment upon the molecular weight distribution of *Aloe barbadensis* gel polysaccharides as determined by size exclusion chromatography upon Sepharose 4B gel. Panels A and B illustrate profiles with polysaccharide from Prep C while Panels C and D show data from Prep D. Panels A and C show profiles of native polysaccharide incubated in the absence of cellulase (A, 10 mg; C, 10 mg). Panels B and D illustrate profiles of cleaved polysaccharide, incubated in the presence of 30 μg cellulase per 100 mg polysaccharide (B, 25 mg; D, 8.4 mg). Polysaccharide was applied to a 2.5×40 cm column in 0.0125% sodium azide and eluted at a flow rate of approximately 10 ml/hour. Hexose content in eluates was determined by Dubois assay and is expressed as $OD_{490}$ nm. The dashed lines illustrate the division of the columns into areas where molecules of >2,000,000 MW elute (first portion, 70–125 ml volume of elution), an intermediate area and the area where molecules with molecular weight <90,000 MW elute (160 to 220 ml of elution).

Figure 9:
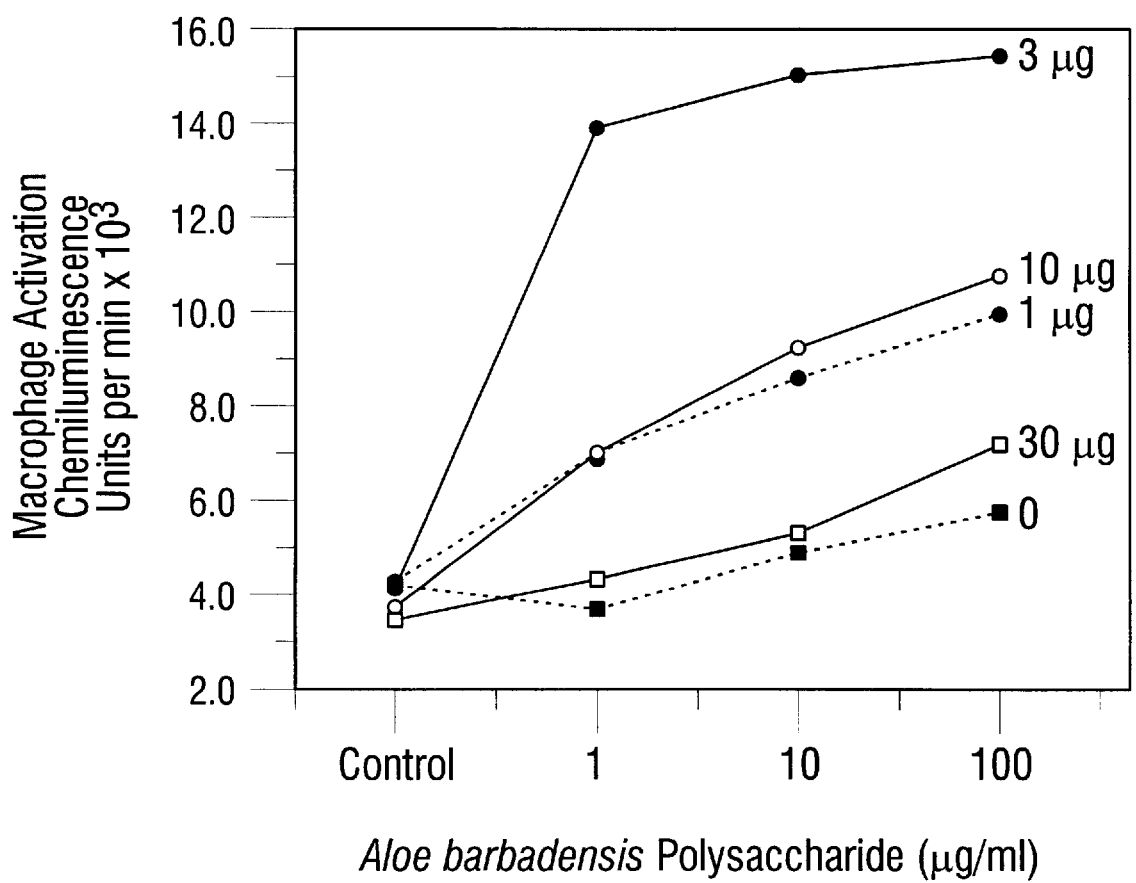

FIG. 9 the effect of cellulase treatment upon the ability of *Aloe barbadensis* polysaccharide to activate a macrophage line in culture. Cells were incubated for one hr in the presence of 1 to 100 μg/ml polysaccharide in DMEM medium. After incubation the cells were washed with PBS and chemiluminescence determined with luminol amplification. The results are the mean of five experiments each conducted in quadruplicate. Isolated polysaccharide was treated with purified cellulase as described in FIG. 4 and subsequently purified by precipitation with ethanol: polysaccharide not treated with cellulase (□); treated with 1 μg cellulase per 100 mg polysaccharide (♦); 3 μg cellulase per 100 mg polysaccharide (■), 10 μg cellulase per 100 mg polysaccharide (○), and 30 μg cellulase per 100 mg polysaccharide (○).

DETAILED DESCRIPTION OF PREFERRED EMBODIMENTS

We teach herein and in the parallel application a family of products that are partially fractionated forms of Aloe, produced by a novel set of processes that allow the controlled production and preservation of the biological activity. The biologically active components appear to be (i) a cytoprotective oligosaccharide of composition different than acemannan and (ii) a activated charcoal absorbable activity separable from aloin and the hydroxy-methylaloins. Hydroxymethylaloins are compounds responsible for color change in Aloe. Acemannan and the alpha-hydroxy acids appear to have no direct biological activity in this system. They may have utility in aiding penetration of the stratum corneum, which function can be replaced by a proper vehicle. Aloe Emodin is very undesirable in this product.

Figure 2:
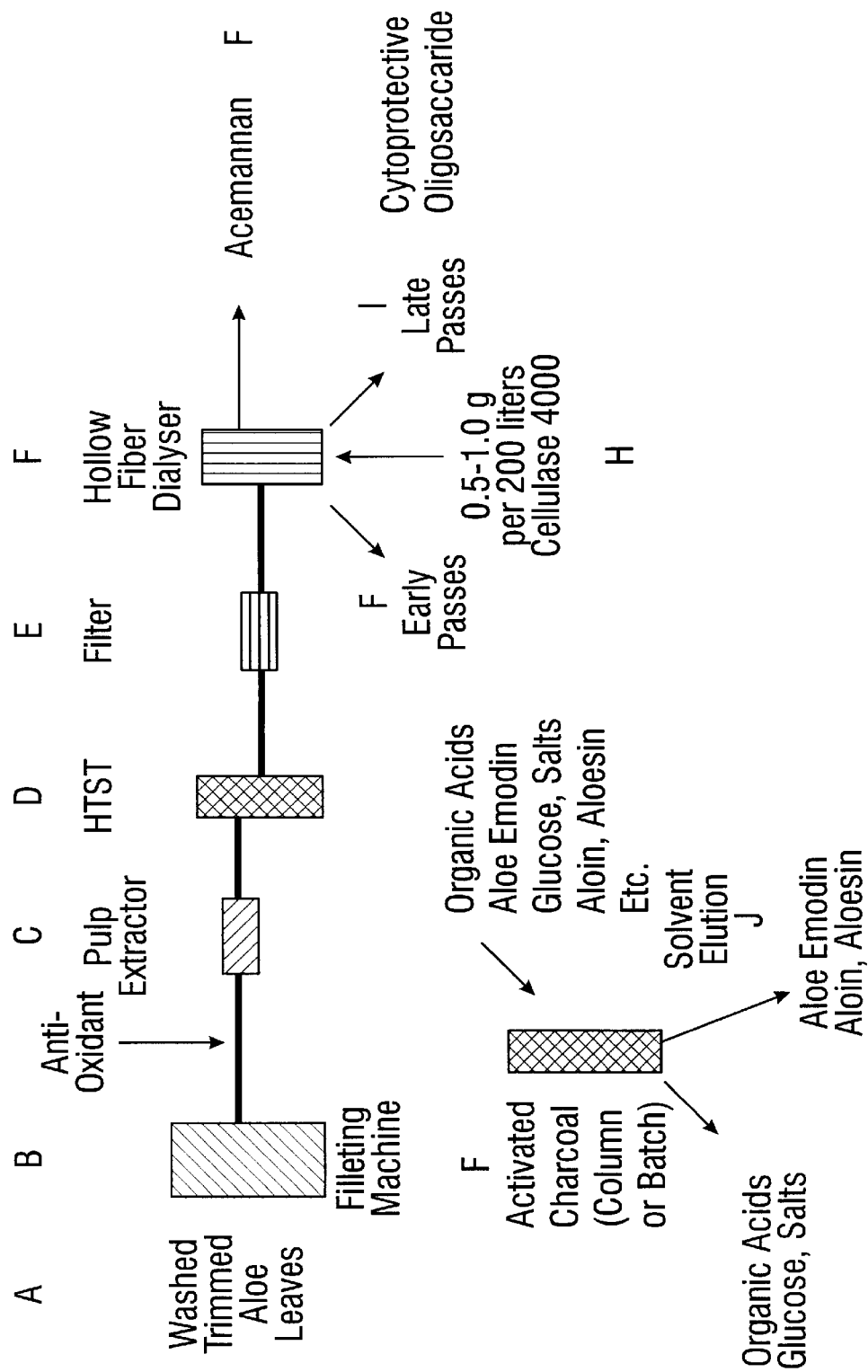
FIG. 2 schematically outlines commercial scale production of the cytoprotective oligosaccharide. Steps A through G are taught in the prior art and are widely employed in commerce. Steps H through J represents the improvements embodied in this (H & I) and the parallel application. After several cycles of passage through the ultrafilter have removed the various desirable and undesirable small molecules, cellulase is added to the retained material. The cellulase splits the cytoprotective oligosaccharide from the native polysaccharide. Since the desired cytoprotective oligosaccharide is less than 5,000 daltons in size it passes through the polysulfone membrane and appears in the dialysate. It is uncontaminated by the cellulase which is retained within the hollow fiber. Acemannan can later be recovered from the retained material by separation from the cellulase. Early pass dialysate, obtained prior to the addition of cellulase can be treated with activated charcoal. Absorbed to the activated charcoal are the factors described in the parallel application which are also desirable for the prevention of ultraviolet radiation-induced injury to the skin immune system. These can be eluted from the activated charcoal as we teach therein.

FIG. 2 outlines a basic schema for production of these materials

This process can be divided into portions covering (i) initial processing, (ii) separation of low molecular weight factors, (iii) generation and separation of the Cytoprotective Oligosaccharide and (iv) potential downstream processing of low molecular weight factors.

Significant factors in the initial processing stream include the following:

1. Whether product is produced from whole leaf or gel, care must be taken to prevent oxidation of the Hydroxymethylaloins to the Red Compound. If possible, oxygen should be excluded from the mill and pulp extractor, purging with nitrogen if feasible. Alternatively, the milling and pulp removal steps should be conducted at low temperature and operations conducted as quickly as feasible. Immediately after the mill, anti-oxidant should be introduced to the stream of ground material.
2. In the past, in order to maximize yield of juice, cellulase is introduced in large quantities early in the stream. We teach the production of a high value product. Therefore, any reduced yield is secondary to product quality. Cellulase is introduced into the stream rather late in order to utilize its value-enhancing property— generation of the Cytoprotective Oligosaccharide from biologically inactive native polysacchaide precursor.
3. Similarly, High Temperature Short Time (HTST) Pasteurization is done as soon as possible to arrest bacterial proliferation. If clogging of the HTST is a significant problem, filtration can be performed before HTST although centrifugal clarification would be preferred.

An important step in the process is the timing of cleavage of native polysaccharide into Acemannan and Cytoprotective Polysaccharide.

In one variant, where a minimally fractionated product is desired, cellulase in moderate amounts (~1.0 to 2.5 grams per 215 liters) is introduced at the start of passage through the hollow fiber dialyser. In this case, Cytoprotective Oligosacchride will be continuously produced—appearing in even the first diffusates removed. If a more highly purified biologically active product is desired, several passages should be performed in the absence of cellulase, removing the bulk of the organic acids, sugar, salts, anthraquinones and chromones. Cellulase can then be added in small amounts (0.5 to 1 gram per 215 liters) and cycling continued.

Preferred for efficient operation of this process is selecting a membrane of proper porosity to allow facile passage of the Cytoprotective Oligosaccharide. Determination of the exact molecular weight of the Cytoprotective Oligosaccharide facilitates this selection.

A primary factor in selecting and controlling the exact process needs to be the relatively rapid, on line, evaluation of the content of the desirable Cytoprotective Oligosaccharide and the highly undesirable Aloe Emodin. If a membrane can be selected that sufficiently hydrophilic to retain Aloe Emodin while passing the activated charcoal factor, this process will be simplified.

In order to minimize oxidation of Hydroxymethylaloin, it may be desirable to purge the water used to charge the hollow fiber dialyser of oxygen prior to use. This may be accomplished by gas purging or vacuum degassing.

The latter stages in processing will depend on the nature of the desired product. If a minimally fractionated product is desired, cellulase is added to the dialyser early in larger amounts as referred to above. In this case, pooled diffusates from the dialyser are the product.

If a more highly fractionated product is desired, lower concentrations of cellulase are used and the stream of difftisate is split. Early diffusates, poor in Cytoprotective Oligosaccharide but rich in Compound 540 and the Aloin/Hydroxymethylaloin complex are diverted into a separate processing pathway. These factors can then be extracted by absorption onto activated charcoal and subsequent elution and separation. Alternatively, the early diffusates can be concentrated and extracted with organic solvents to yield the desired fraction.

A third possibility is to make Oligosaccharide from low anthraquinone gel and supplement this product with the activated charcoal absorbed factor extracted from rind and anti-oxidants.

Which ever of these possible processing scenarios is selected, process control will be heavily dependent on the ability to rapidly and accurately measure the critical desired analytes: the Cytoprotective Oligosaccharide, and the activated charcoal factor and also measure undesirable components: the Hydroxymethyl-aloin compound responsible for color change and highly undesirable Aloe Emodin.

The present invention involves a fraction of *Aloe barbadensis* that can be applied for therapeutic purpose to the skin subsequent to exposure to UVB radiation. Exposure of the skin to UVB radiation causes suppression of the skin immune system. Suppression of this immune response is thought to predispose to the growth of sun-induced tumors. The present invention also involves prevention of damage to the skin immune system and comprises:

(i) A composition of matter of the biologically active product (a glucose-rich, mannose-containing oligosaccharide of MW~1,000–5,000 daltons, one of two products cleaved by cellulase from a precursor block polysaccharide—the native polysaccharide of Aloe—the other product being the molecule "Acemannan" which is biologically inactive in this system).

(ii) The process of preparing this product by digestion of native *Aloe barbadensis* gel by a combination of ultrafiltration through hollow fibers under pressure and treatment with cellulase wherein the enzyme cellulase and other cleavage materials ("Acemannan") remain within the hollow fiber while the product oligosaccharide passes through. This process can be modified, by virtue of the timing wherein the cellulase is added, to produce the desired oligosaccharide with high efficiency and moderate purity on an industrial scale.

(iii) The utility of a preparation with composition of matter (i) prepared by process (ii) in the treatment of UVB-induced injury to the skin immune system.

Native *Aloe barbadensis* gel produced under the most careful conditions is minimally active, immediately after production, in preventing UVB-induced damage to the skin immune system. Upon storage of the gel at −20° C. for a period of months, the gel is "activated" to a protective state. This process of "activation" can be accelerated by the use of low to moderate (0.5 to 2.5 grams "cellulase"/215 Liters of gel) concentrations of commercial "cellulase".

The use of "cellulase" of utility for reducing pseudoplasticity and increasing yields of material is well described in the Aloe industry (Coats patent and numerous prior uses). This is the first use of cellulase with intent of producing biologically active product. If the method of Coats is followed inactive product results. However, Aloe gel prepared by the basic method described herein may lose its biological activity with time.

Figure 1:
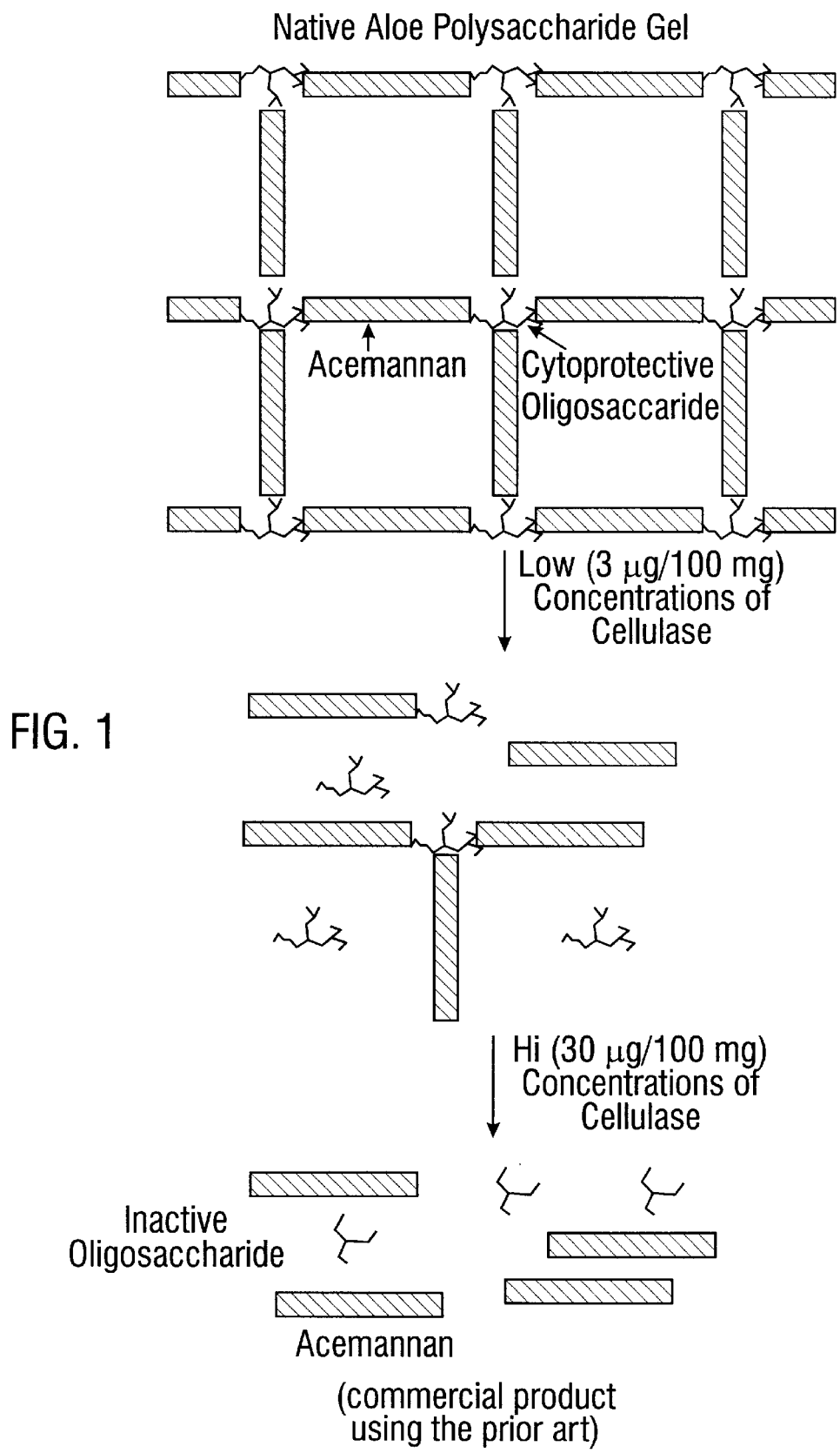
FIG. 1. schematically designates the proposed schematic structure for the Aloe barbadensis native predominant polysaccharide and designates possible events during conmmercial processing or endogenous decay. The molecule exists as a block copolymer rather than the homopolymer previously taught. The blocks consist of (i) ~12,000 dalton units of heavily acetylated mannan with β 1-4 linkages connected by a second block (ii) of a non-acetylated glucose and galactose containing saccharide. This second block is of molecular weight 1,000 to 5,000 daltons and is predominately β 1-4 linked. However because of its structure it is far more sensitive to β 1-4 glycosidases than is the acetylated mannan. In the native form, the block polymer has neither the biological activity characteristic of the acetylated mannan (activation of phagocytic cells) nor of the linking region (cytoprotection). After harvest, endogenous β β1-4 glycosidases begin to break the native block polymer down, decreasing pseudoplasticity and resulting in liberation of mannan and oligosaccharide. At this point biological activity is generated. The same effect can be achieved with the use of very low concentrations of commercial cellulase. The optimal concentration of pure cellulase to pure polysaccharide is less than 3 mg cellulase per 100 mg polysaccharide. In commercial practice this equates to less than 3 grams of commercial cellulase to 215 liters of absolutely fresh *Aloe barbadensis* gel. If the process is allowed to proceed too far, the highly cellulase-sensitive oligosaccharide is further cleaved producing a biologically inactive product. These deleterious concentrations of cellulase and times of incubation are typical of the prior state of the art. The more cellulase-resistant acetylated mannan may be unaffected by conditions that degrade the cytoprotective oligosaccharide. This results in a product that is deficient in the desired biological activity (protection of the skin immune system from suppression by ultraviolet radiation) which is typical of the currently available commercial products.

Elucidation of the composition of matter of the active ingredient, an oligosaccharide cleaved from the native, biologically inactive precursor molecule gives the structure illustrated in the FIG. 1. These biochemical studies have helped the present inventors design the production scheme illustrated herein.

In a development of our method, native Aloe gel is treated with cellulase while circulating through a hollow fiber dialyser with polysulfone membranes of molecular weight cutoff 5,000 daltons. This removes the cytoprotective oligosaccharide into the dialysate before it can be further cleaved by the cellulase and inactivated. This allows the simultaneous generation and partial purification of the factor if the system is allowed to cycle for some time (to remove the low molecular weight components of the Aloe gel) before the cellulase is added to begin cleavage.

McAnalley suggests that the structure of the native polysaccharide of *Aloe barbadensis* gel is a homopolymer of (2,3-Acetylmannose β1-4 6-Acetylmannose)$_n$ of molecular weight 45,000–180,000 daltons ("Acemannan"). McAnalley claims that this molecule contains all the biological activities of Aloe. The present invention shows (see FIG. 1) that the native polysaccharide of *Aloe barbadensis* gel is a highly pseudoplastic, biologically-inactive, block copolymer of molecular weight >2,000,000 daltons consisting of subunits of "Acemannan" connected together by highly cellulase-sensitive subunits of an oligosaccharide of non-"Acemannan" structure (glucose-rich, mannose-containing, non-acetylated) of approximately 5,000 daltons. Cleavage of the native polysaccharide with low concentrations of cellulase liberates the ethanol-soluble biologically active (UVB protective, cytoprotective) oligosaccharide from the ethanol-insoluble, now-biologically-active (phagocyte stimulation) "Acemannan".

These differences in claimed composition of matter also lead to a novel method of processing and novel analytical chemical tests for process control.

Coats indicates that Aloe can be processed via treatment with cellulase the utility of which is increased yield of crude gel and decreased pseudoplasticity. Coats did not appreciate the utility of cellulase in generating biological activity. Furthermore, his claim that 50 grams of cellulase per 215 Liters of Aloe gel has utility is without merit with regard to biological activity. The present invention involves showing that even 5 grams of cellulase per 215 Liters quickly destroys biological activity.

The following examples illustrate preferred embodiments of the present invention.

EXAMPLE 1

Activation and Decay of An Activity Restoring Contact Hypersensitivity (CHS) to DNFB in Mice Exposed to UVB Radiation Production and Activity of Native Gel Previous experiments suggested that *Aloe barbadensis* gel was capable of reversing the damage to the skin immune system induced by exposure to ultraviolet radiation (Strickland et al. 1994). However this activity is labile and was lost upon storage of the lyophilized powder. Attempts were made to slow this decay of activity by producing *Aloe barbadensis* gel under conditions of very high sanitation. These conditions would yield gel that closely approximates the native form within the plant. Steps involved are:

(i) very rapid (1–2 hours) processing of leaves after harvest, (ii) thorough sanitization of the external surfaces of leaves and trimming of necrotic or damage portions of leaves to remove bacteria, (iii) exteme care in removal of rind such that bacteria resident in rind did not contaminate the gel and anthraquinone-containing vascular material was excluded, (iv) chilling of gel immediately after pulp removal and transport in the cold to minimize bacterial proliferation.

These conditions are not novel and in fact encompass common-sense procedures obvious to any one skilled in the art. Although they are claimed frequently in almost all letters patent in the field of Aloe technology they are seldom employed in industry because manufacturers of consumer products do not require material of this quality for their products. Previously explicated technologies that measure and claim biological activity do not require starting materials of this quality.

This native *Aloe barbadensis* gel was found to be highly pseudoplastic. As such it is difficult to impossible to concentrate. Without concentration it is economically unfeasible to freeze dry and thereby put into a form suitable for international commerce. For purposes of experiment, this native *Aloe barbadensis* filleted gel was lyophilized directly in the unconcentrated pseudoplastic form. It was assayed for biological activity using the following test.

Protocol for Testing Aloe Materials for Protection of the Skin Immune System Against Suppression By Ultraviolet Radiation C3H female mice were anesthesized and their shaved abdomens were exposed to 2 kJ/m² Ultraviolet B Radiation (UVB). Immediately after exposure a unbuffered solution of Aloe, reconstituted to 0.5 g/dl in water, was applied to the irradiated abdominal skin. After a four day recovery period, the mice were immunized by application of dinitrofluorobenzene (DNFB) to the previously irradiated skin. Seven days later, a period of time sufficient for the immune response to develope, contact hypersensitivity (CHS) to DNFB was measured. This was done by painting a challenge dose of DNFB on the ears (which had been protected from the irradiation by a covering of aluminum foil) and measuring the swelling the next day. Controls included; (i) animals which received no UVB injury, Aloe treatment, or immunization but were challenged (Unsensitized—Negative Controls), (ii) animals which received no UVB injury or Aloe treatment but which were immunized with DNFB (Positive Controls) and (iii) animals which were UVB irradiated and then immunized but which received no Aloe treatment (Fully Suppressed, No Rx Controls). Data was recorded as ear swelling (in mm×10⁻²) as the average of both ears. All experiments were conducted with groups of 5 mice. This test system is referred to as the CHS/UVB test system.

In order to more clearly discern therapeutic effect above and beyond the usual variation that is observed from experiment to experiment, the data was transformed to normalize values as we have previously published (Strickland et al. 1994). The Positive Control was normalized for each experiment to 100% and the Fully Suppressed No Rx Control was Normalized to 0% for each experiment. Therefore the data in Table I are presented as percent protection. Complete suppression of the immune response (No Rx Control) is expressed as 0% and complete restoration of immune response is expressed as 100%.

Biological Activity of Native *Aloe barbadensis* Gel

Initially, upon reconstitution with pure water, the lyophilized psuedoplastic native Aloe gel possessed little restorative activity in the CHS/UVB test system (Table I, 3 weeks of storage prior to reconstitution, 12±6% protection). With storage of this material prior to reconstitution, activity in the CHS/UVBsystem increased ("activation"). Significant protection was obtained at 4 weeks (Table I, 21±5%) and 6 weeks (Table I, 32±10% protection) However, this activation process was irregular (as is expected from a naturally occuring process) and decay eventually still occurred (Table I, 6 weeks).

TABLE I

Effect of Cellulase Dose Upon Time Dependent Decay of Protective Activity of Crude Aloe Gel CHS to DNFB in Mice Exposed to 2 kJ/m² UVB

| | % Restoration of CHS by Aloe (0.5% in water)* Concentration of Cellulase (g per 215 liters) | | | |
|---|---|---|---|---|
| Time After None Preparation | 0.5–1.5 | 2.0–2.5 | 5.0 | |
| 3 Weeks | 12.2 ± 5.5% | 15.7 ± 5.7% | 21.7 ± 6.4% | 24.2 ± 8.6% |
| (n) | (10) | (20) | (15) | (10) |

TABLE I-continued

Effect of Cellulase Dose Upon Time Dependent Decay of Protective Activity of Crude Aloe Gel CHS to DNFB in Mice Exposed to 2 kJ/m² UVB

| | % Restoration of CHS by Aloe (0.5% in water)* Concentration of Cellulase (g per 215 liters) | | | |
|---|---|---|---|---|
| 4 Weeks | 21.0 ± 5.2% | 26.8 ± 15.7% | 53.0 ± 9.5% | 48.4 ± 8.5% |
| (n) | (10) | (5) | (15) | (10) |
| 5 Weeks | 31.9 ± 10.4% | 46.0 ± 7.9% | 62.0 ± 7.6% | 55.3 ± 18.1% |
| (n) | (10) | (15) | (18) | (10) |
| 6 Weeks | 4.7 ± 10.5% | 31.0 ± 9.1% | 18.6 ± 6.0% | 3.3 ± 6.6% |
| (n) | (10) | (20) | (15) | (10) |

ªCalculated for each animal by normalization between the No Rx Controls and Positive Controls for each experiment. Data expressed are the Mean ± Standard Error of the Mean for the number of mice indicated.

Treatment of *Aloe barbadensis* Gel with Cellulase

At approximately the same time as the experiments described above, we were exploring the use of commercial "cellulase" preparations as taught by Coats (U.S. Pat. No. '811) in an attempt to reduce psuedoplasticity so that the Aloe gel could be economically concentrated by risingfalling thin-film evaporation prior to freeze drying. We found that the use of "Cellulase" as taught by Coats did reduce psuedoplasticity but when employed as he taught it, 99%+ of the polysaccharide was destroyed. Thus for our purposes, the method was without utility. However, much to our supprise, we noted that when amounts of "cellulase" one tenth the amount taught by Coats was employed, the activation process occurred more rapidly. This finding of activation of Aloe by a glycosidase was unprecedented in the literature. Therefore, in order to precisely define this phenomen of activation and decay a series of systematic experiments were conducted.

Two liter portions of unprocessed native Aloe gel were incubated under ambient laboratory conditions with varying (0.5 g to 5 g per 215 liters) amounts of commercial "cellulase". After incubation was completed the material was lyophilized and stored at −20° C. until assay of biological activity. This production experiment was repeated three times using separate, fresh lots of *Aloe barbadensis* native gel. Each of these Aloe materials were tested on three occasions after preparation according to the CHS/UVB test system (Table I). The data demonstrate that "cellulase" causes an increase in biological activity but that this activity is labile and is destroyed by higher doses of "cellulase".

Data Analysis

The analysis of the data is complicated since there are many sources of variation: (i) animal to animal variation within a single experiment, (ii) time to time variability (both activation and decay of biological activity and experiment to experiment variation), (iii) lot to lot variability in the raw materials, and (iv) actual therapeutic effect. Normalization of results to positive and negative controls can be used to correct for experiment to experiment variability but can introduce artifacts into the data base. Therefore, statistical analysis was first performed on raw data by Repeated Measures ANOVA with treatment as one independent variable and time after preparation of the Aloe material as the second independent variable (Repeated Measure).

In general, there was the expected degree of animal to animal variation, variability in irritancy and sensitization from experiment to experiment and a certain variation in the degree to which the cutaneous immune response was suppressed by UVB from experiment to experiment. All three preparations of *Aloe barbadensis gel* displayed with "cellulase" a significant degree of protection to the skin immune response after UVB injury (Table 2, Rx or Therapeutic Effect). However, there was a highly significant degree of experiment to experiment variation exclusive of the inherent variability observed in the Negative Controls, Positive Controls and No Rx suppressed controls. This constitutes the activation and decay phenomenon wherein soon after preparation Aloe is poorly active, then activity increases with time and activity subsequently decays.

TABLE 2

Statistical Analysis of Effect of Cellulase Dose Upon
Protective Activity of Crude Aloe Gel
Raw Data - CHS to DNFB in Mice Exposed to 2 kJ/m$^2$ UVB
Significance of Restoration of CHS by Aloe (0.5% in water)*
Concentration of Cellulase (g per 215 liters)

| Preparation | | None | 0.5–1.5 | 2.0–2.5 | 5.0 |
|---|---|---|---|---|---|
| A | Rx Effect | p = 0.026 | Not Done | p = 0.0001 | p = 0.001 |
|   | Time Effect | p = 0.0001 | p = 0.0001 | p = 0.0001 | p = 0.0001 |
| B | Rx Effect | p = 0.06 | p = 0.005 | p = 0.008 | p = 0.0001 |
|   | Time Effect | p = 0.003 | p = 0.0002 | p = 0.0001 | p = 0.0001 |
| C | Rx Effect | Not Sigificant | Not Sigificant | p = 0.003 | Not Sigificant |
|   | Time Effect | p = 0.0015 | p = 0.001 | p = 0.008 | p = 0.0002 |

<sup>a</sup>Calculated for each animal by normalization between the No Rx Controls and Positive Controls for each experiment. Data expressed are the Mean ± Standard Error of the Mean for the number of mice indicated.

Although this activation and decay phenomenon was observed with native Aloe gel, statistical analysis indicated that the effect was even more pronounced with cellulase treatment (positive statistical effect for interaction). Thus, both the therapeutic effect and "activation and enhanced decay" with "cellulase" are observed with the raw data.

Normalization allows us to numerically more clearly see the effect of "cellulase" treatment upon UVB/CHS restorative activity. Statistical analysis yielded identical probabilities of significant treatment effect (Rx) with raw and normalized data. Thus, the process of normalizing the data did not introduce any artifact into the statistical analysis. Averaged over all time periods, "cellulase" treatment caused a two to five fold increase in the ability of *Aloe barbadensis* gel to protect the skin immune system subsequent to injury. Evaluating data from all times, activation was stongest at intermediate doses of "cellulase" (2.0 to 2.5 g per 215 liters concentration). In two of three preparations, the use of a higher dose of cellulase (5.0 g/215 liters) resulted in lesser protective activity. ANOVA suggested (significant interaction at high cellulase dose) that this activation effect was strongly time dependent.

Normalization makes clear the discrimination of the time effect of activation and decay (Table 1). In this case we have displayed the data as time after preparation, averaging the different preparations at similar time points. Data from 9 weeks post preparation is omitted because the numbers of animals are too small for meaningful comparison. *Aloe barbadensis* native gel, untreated with exogeneously-added cellulase undergoes a 2.5 fold activation with time before protective ability decays. At low doses of cellulase (0.5 to 1.5 g/215 liters), there is a three-fold activation and by 6 weeks the activity is just beginning to decline. Moderate and high doses of cellulase yield Aloe gel that is already significantly activated by the time of the first experiment (3 weeks after production). Because these materials are already partially activated, the 2 to 3 fold magnitude of the increase in activity is less striking than the absolute values of the protection. At high dose, the drop off in activity with time is precipitous and by 6 weeks activity is lower than that with 0.5–1.5 g/215 liters.

In summary, there is a spontaneous activation of CHS/UVB protective activity in native *Aloe barbadensis* gel produced under scrupulous process conditions and stored lyophilized at −20° C. This activity is maximal 4 to 5 weeks after production and is followed by a decline at 2 to 3 months after production. Higher levels of activation are achieved by use of commercial "cellulase". Judging by the activity 4 to 5 weeks after preparation, the optimum dose of "cellulase" is 2.0 to 2.5 g/215 liters. However, the higher the dose of cellulase, the quicker the loss of activity at 2 months. Viewed in the most simplistic fashion, this suggests that a polysaccharide is being activated by a glycosidase but that excess enzyme treatment is breaking down the active molecule.

EXAMPLE 2

Effect of "Cellulase" Treatment Upon Phagocyte Activiting Activity

The effect of "cellulase" in the experiments above suggested but do not prove that the activity effects observed with native *Aloe barbadensis* gel are generated by cleavage of polysaccharides. We therefore further explored the concept that generation of biological activity in Aloe could be produced by cleavage of the native polysaccharide. As presented in the Related References section, one of the biological activities of the classically described Aloe mannan polysaccharide is activation of phagocytic cells. We therefore determined if the phenomenon of activation and decay by glycosidases could be also observed using in vitro cultures of phagocytic cells as a test system for biological effect.

Figure 3:
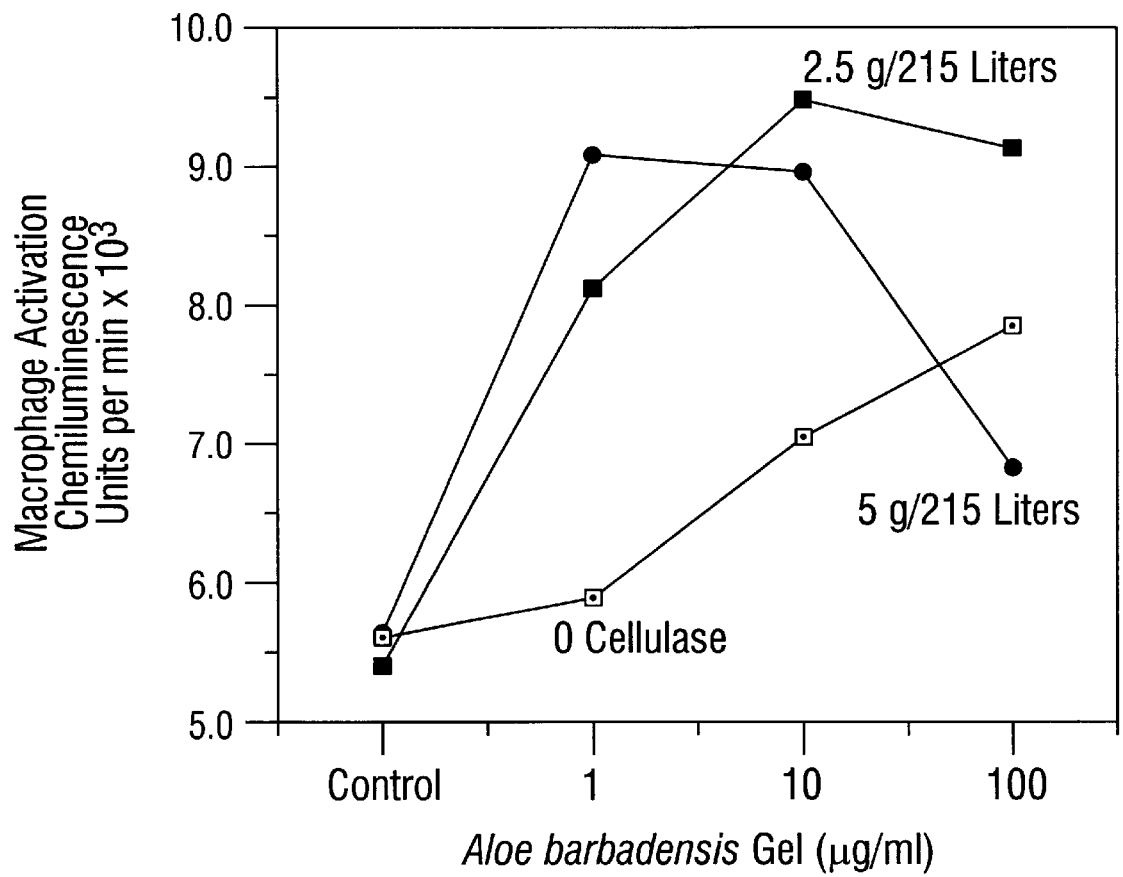
FIG. 3. illustrates the effect of cellulase treatment upon the ability of *A. barbadensis* gel to activate a macrophage cell line in culture. Cells were incubated for 1 hour in the presence of 1 to 100 mg/ml of gel in DMEM media. After incubation the cells were washed with PBS and chemiluminescence determined with luminol amplification. The results are the mean of 5 experiment each conducted in quadruplicate. Polysaccharide was treated with cellulase as described in Example 2. Results with untreated gel are indicated by the line with open squares. Results of treatment at a cellulase concentration of 2.5 gram per 215 liters is indicated by closed squares and treatment at 5 g per 215 liters by closed circles.
Figure 4A:
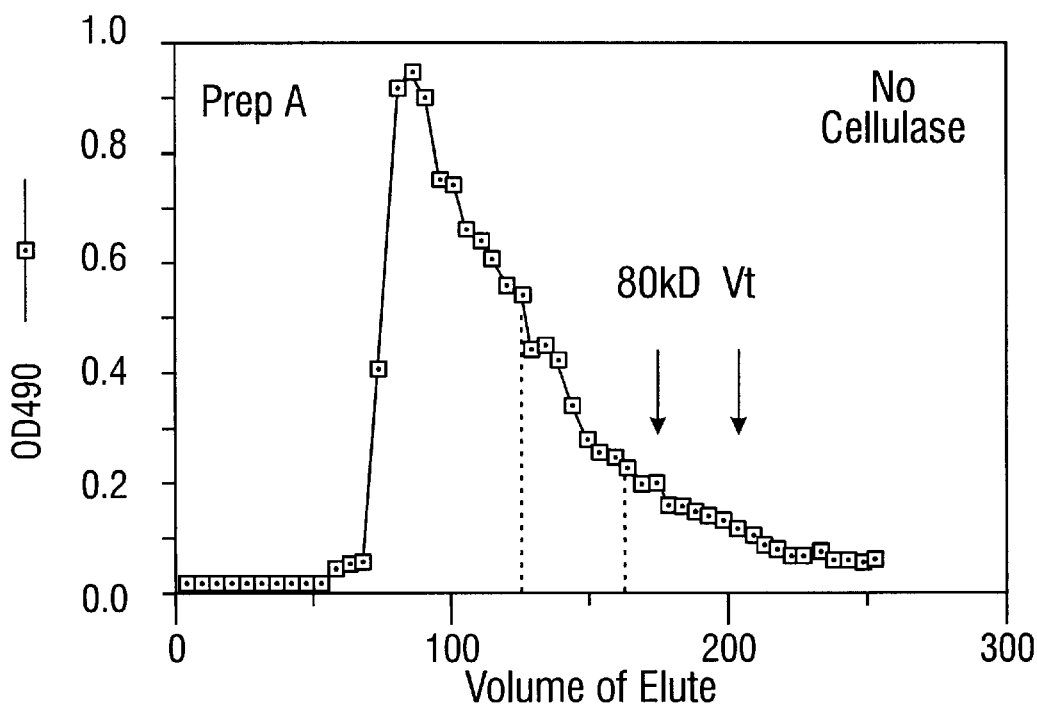
FIG. 4. describes the effect of "cellulase" treatment of native gel upon the molecular weight of the polysaccharides isolated from native gel. The materials analysed were from Table 2 in Example 1. Polysaccharide was isolated by exhaustive dialysis in the cold followed by precipitation with 80% (v/v) absolute ethanol. Polysaccharide (5 to 30 mg) was applied to a 2.5×40 cm column of Sepharose 4B in 0.0125% (w/v) sodium azide and eluted at a flow rate of approximately 10 ml/hr. Hexose content in eluates was determined by Dubois assay and is expressed as $OD_{490\ nm}$. The dashed lines illustrate the division of the column eluates into areas where molecules of >2,000,000 daltons elute, an intermediate area and the area where molecules with molecular weight <90,000 daltons elute. Rechromatography of these (<90,000) materials upon a size exclusion column more appropriate to their molecular weight (Biogel P-150) indicates they have a molecular weight of 12–15,000 daltons.
Figure 4B:
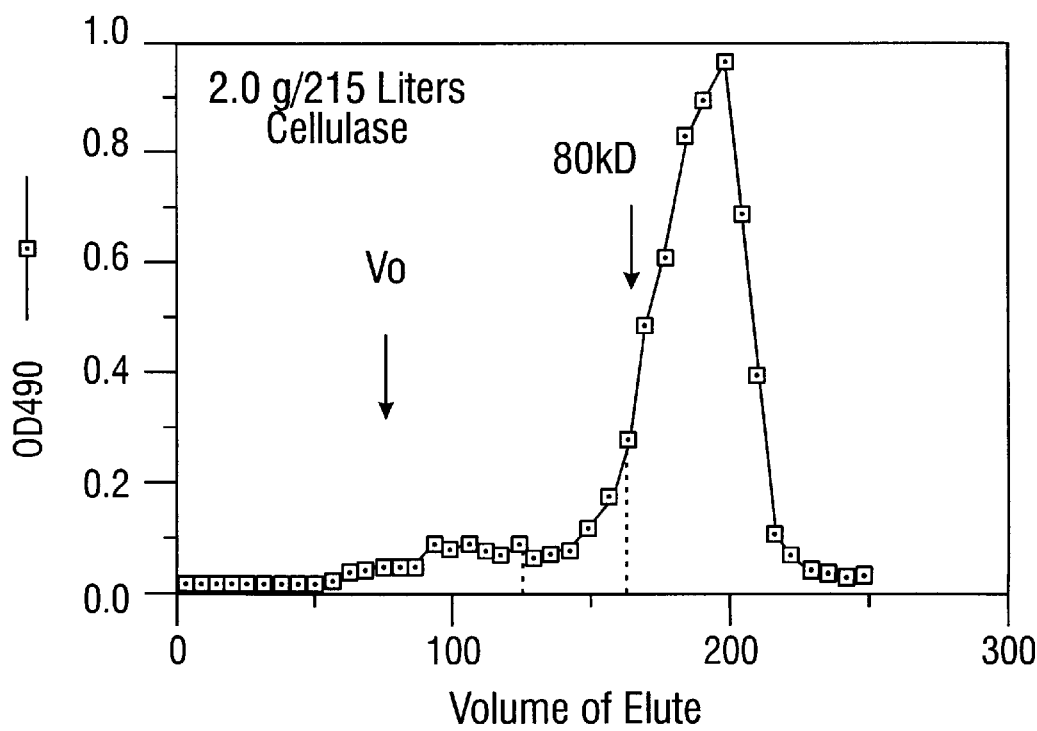
Figure 4C:
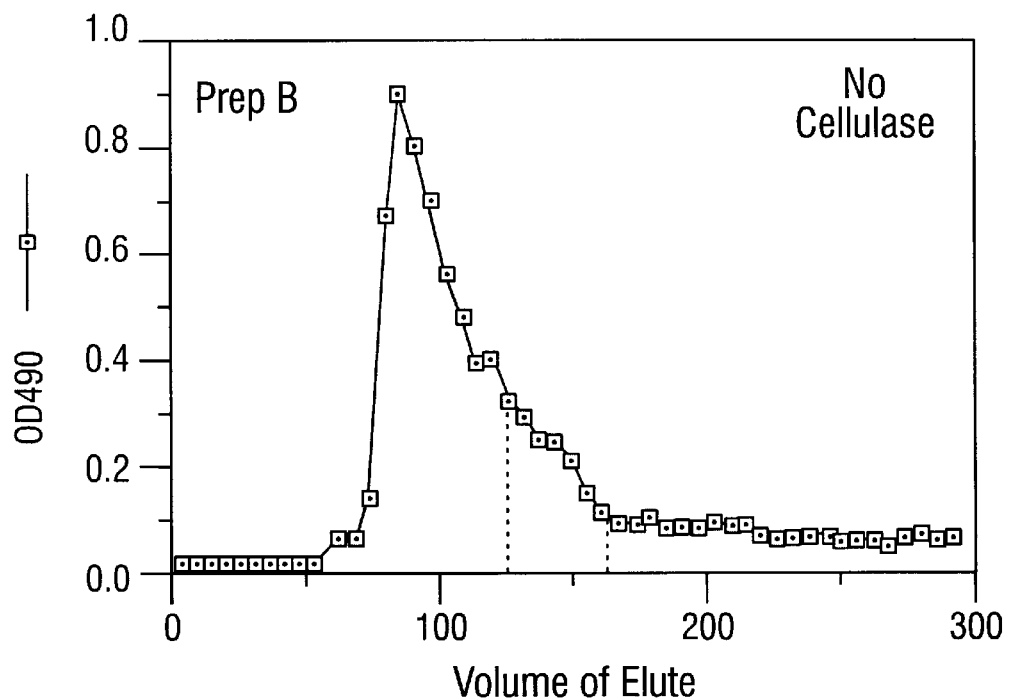
Figure 4D:
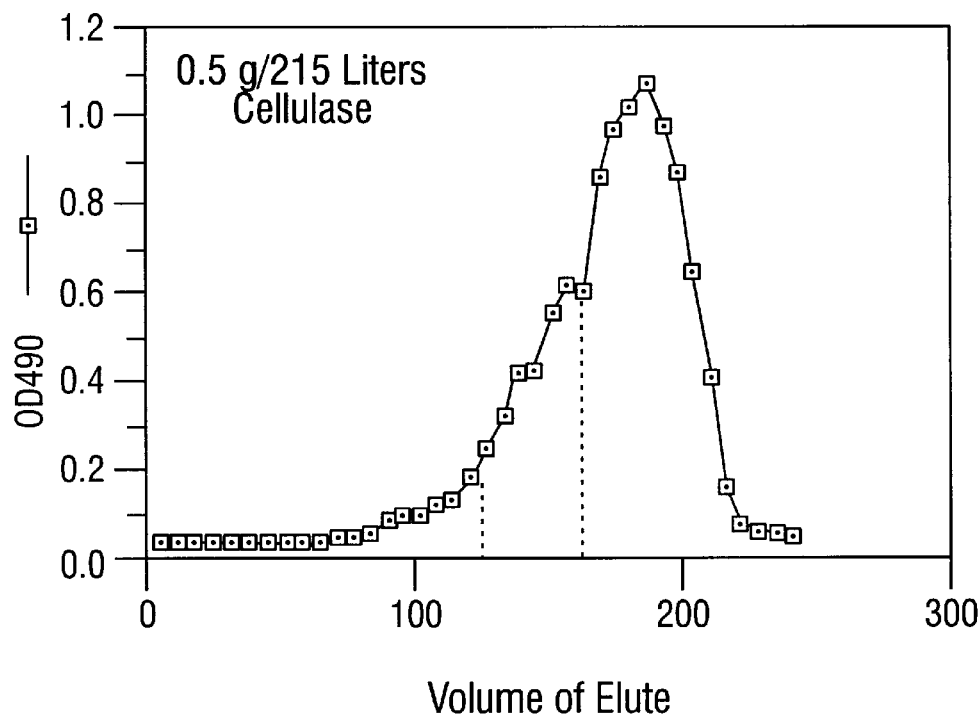
Figure 4E:
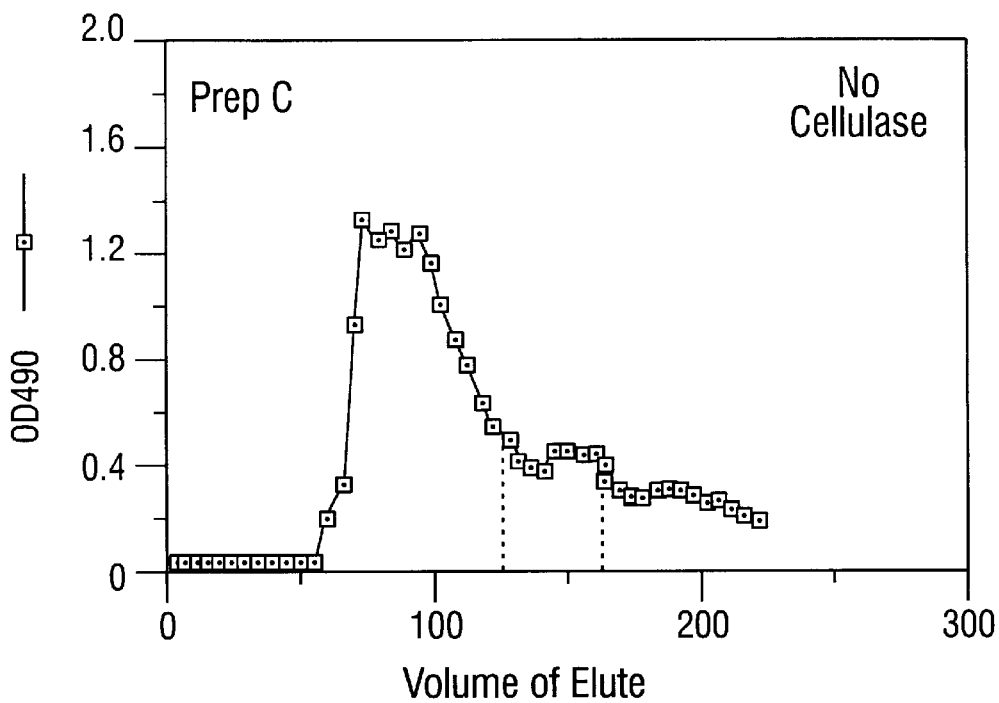
Figure 4F:
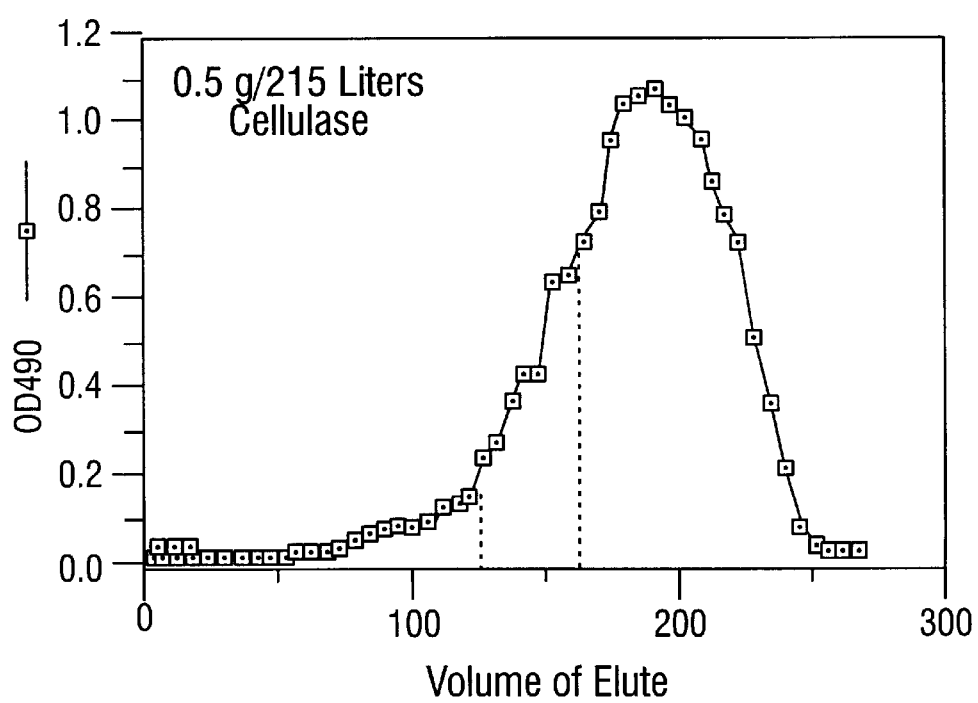

FIG. 3 illustrates the results when Aloe gel from preparation A in Table 2, treated with various concentrations of commercial "cellulase" was incubated with cells from a macrophage line. The degree of macrophage activation was quantitated by the increase in hexose monophosphate shunt using a chemiluminescent probe. Native Aloe gel, unactivated by "cellulase" yeilded weak activity with maximum effect at a concentration of 100 mg/ml. Treatment with moderate doses (2.0 to 2.5 g/215 liters) of "cellulase" yeilded a 100 fold more potent preparation (8,000 units at 1 mg/ml versus 8,000 units at 100 mg/ml). The data at 2.0 and 2.5 g/215 liters were identical and therefore the data for 2.0 g/215 liters were omitted for the sake of clarity. Treatment of Aloe gel with high dose (5 g/215 liters) "cellulase" gave an activation similar to that observed with lower concentrations of "cellulase" when 1 and 10 mg/ml of Aloe were tested. However, testing of larger amounts (100 mg/ml) Aloe demonstrated diminished activity (22% less). This is reminescent of the accelerated decay of the CHS/UVB biological activity at high "cellulase" dose.

These experiments confirm that (i) low anthraquinone *Aloe barbadensis* gel produced under stringent sanitation and prepared under conditions where enzymatic activity is lessened, has comparatively little biological activity. Furthermore, (ii) treatment of this native Aloe gel with commercial glycosidase results in a 100 fold increase in a biological activity classically ascribed to a polysaccharide. The generation of biological activity was biphasic—high concentrations of commercial "cellulase" resulted in diminished biological activity at high doses of crude Aloe gel. These findings are consistent with cellulases causing its effect by acting on a polysaccharide.

EXAMPLE 3

Analysis of Polysaccharides of *Aloe barbadensis* gel After Treatment With Commercial Cellulase The above biological findings point to polysaccharides as molecules likely to be altered during the activation and decay process. Therefore, the content and composition of the *Aloe barbadensis* polysaccharides in native gel and in gel treated with "cellulase" was examined. Table 3 gives the results of total polysaccharide content of Aloe treated with various concentrations of "cellulase". Treatment with low (0.5–1.5 g/215 liters) to moderate (2.0–2.5 g/215 liters) concentrations of "cellulase" caused a slight (22%) decrease in the content of polysaccharide determined as alcohol precipitable hexose. Because of the large degree of variability in the content of polysaccharide in native gel (4 to 25%), this difference can only be regarded as marginally significant. Treatment of Aloe gel with higher (5 g/215 Liters) concentrations of commercial "cellulase" resulted in a striking (56%) decrease polysaccharide content.

TABLE 3

Polysaccharide Content of *Aloe barbadensis* gel[a]

| Preparation | Cellulase Treatment (g/215 Liters) | | | |
|---|---|---|---|---|
| | 0 | 0.5–1.5 | 2.0–2.5 | 5.0 |
| ARF'94G | 18 ± 1% | | 16 ± 1%[b] | 6 ± 1% |
| ARF'94H | 25 ± 1% | 14 ± 1%[c] | 11 ± 2%[b] | 11 ± 1% |
| ARF'94J | 4.1 ± 0.2% | 7.2 ± 0.2% | 6.6 ± 0.3% | 3.6 ± 0.3% |
| Mean ± S. E. M. | 15.7 ± 6.1% | 12.2 ± 1.7% | 12.2 ± 1.9% | 6.9 ± 2.2% |
| % Decrease With Cellulase | | 22.3% | 22.3% | 56.1% |
| (n) | (3) | (4) | (5) | (3) |

[a]Determined by the method of Pelley (1995) as alcohol precipitable hexose. Values are alcohol precipitable hexose as a percentage of total mass and unless otherwise indicated are the result of a single assay with hexose determination (mean ± range) done in duplicate. Materials are from preparations in Example 1.
[b]Two assays, results are the mean ± range of the two assays.
[c]Three assays, results are the mean ± range of the three assays.

Treatment with "cellulase" not only affected the content of crude polysaccharide, but had a far more profound effect upon the form of the polysaccharide (FIG. 4). The molecular weight distribution of polysaccharides was assessed by size exclusion gel permeation chromatography. Monosaccharides and oligosaccharides were removed from samples of crude Aloe gel by either exhaustive dialysis, alcohol precipitation or a combination of the two processes. Crudely purified polysaccharide was then separated into classes according to size exclusion using columns of Sepharose 4B. The hexose content of each fraction was quantitated using the Dubois phenol sulfuric acid assay. The chromatogram was divided into three regions based on the profile and the elution of polysaccharide mariers of know molecular weight. The molecular weights derived from this analysis must be regarded as tentative because size exclusion chromatography measures the Stokes radius of the molecule. Polysaccharides, unlike globular proteins, are know to have significant axial asymmetry and therefore size exclusion MW are inaccurate. However, the gel used—Sepharose 4B, more accurately demonstrates the high molecular weight of the native polysaccharide than those employed in the previous art.

As seen in FIG. 4 and summarized in Table 6, native *Aloe barbadensis* gel produced by the careful attention to speed, cleanliness and slow temperature has polysaccharide that differs greatly in its molecular weight distribution from that of the prior art. This polysaccharide is almost exclusively in forms greater than 2,000,000 daltons It should be noted that this high molecular weight, native form of the gel is biologically poorly active in the classic assay for "Acemannan" biological activity (activation of phagocytic cells) and in protection of the skin immune system against damage by radiation. Treatment of native Aloe gel with even the lowest concentration of "cellulase" in every instance converts the polysaccharide to a lower molecular weight form consistent with the structure A reviewed above. Our *Aloe barbadensis* gel consists of only 18±4% polysaccharide consistent with structure A while treatment with the lowest doses of "cellulase" employed yields gel wherein 78±4% of the polysaccharide is in the form described for structure A.

TABLE 6

Molecular Weight Distribution of *Aloe barbadensis* gel Polysaccharide[a]

| Preparation | Molecular Weight Class[b] | | | Cellulase |
|---|---|---|---|---|
| | <2,000,000 MW | Intermediate | 90–45,000 MW | |
| A | 65% | 22% | 13% | None |
| | 6% | 7% | 87% | 2.0 g/215 Liters |
| B | 66% | 19% | 15% | None |
| | 5% | 23% | 72% | 0.5 g/215 Liters |
| C | 57% | 18% | 25% | None |
| | 6% | 18% | 76% | 0.5 g/215 Liters |
| Mean ± S. E. M. | 63 ± 3% | 20 ± 1% | 18 ± 4% | None |
| Mean ± S. E. M. | 6 ± 1% | 16 ± 5% | 78 ± 4% | Yes |

[a]Determined by partially purifying the material in order to remove monosaccharides and oligosaccharides. Molecular weight distributions were determined by size exclusion gel permeation chromotography on Sepharose 4B (2.5 × 40 cm) columns using a 0.0125% sodium azide buffer.
[b]Total Hexose determined by Dubois assay in the respective regions: <2,000, 000, between the void and the volume corresponding to one-third the volume between the void volume and the total working bed volume of the column; Intermediate, the region between <2,000,000 region and the lower molecular weight region; 90–45,000 MW, the region beginning with the volume corresponding to two-thirds the volume between the void volume and total working bed volume of the column and encompassing the total working bed volume of the column. These three areas are demarked by the vertical dashed lines in FIG. 4

It should be noted that the transformation of polysaccharide from the native form into the "Acemannan" form is associated with the appearance of the classical "Acemannan" biological activity (phagocyte activation).

In native *Aloe barbadensis* gel (produced under CONDITIONS where bacterial contamination is minimal, contamination with anthraquinone-rich and enzyme-rich rind is minimized, and processed under conditions where enzymatic activity is reduced) biological activity is low. This protocol produces *Aloe barbadensis* gel wherein the polysaccharide is in a high (<2,000,000 MW) molecular weight configuration. Native gel spontaneously activates upon storage to produce a material with a significant ability to restore, with topical application, to the murine skin immune system, the ability to respond to contact allergens usually lost after UVB irradiation. This UVB restorative active, however, is labile and is lost upon prolonged storage.

Treatment of native *Aloe barbadensis* gel with commercial "cellulase" activates the CHS restorative activity in a controlled fashion directly related to the concentration of "cellulase" employed. This controlled activation is accompanied by the conversion of the native very high molecular weight polysaccharide to a lower molecular weight (10–15 kD) form. Concomitantly, the gel acquires the ability to stimulate, in vitro, mammalian phagocytic cells. However, at the highest dose of "cellulase" employed (5.0 g/215 liters) biological activity is more labile than in native form.

These findings suggest the existence of a novel molecule—a highly pseudoplastic, very-high molecular weight, biologically-inert precursor molecule. Treatment of this native precursor molecule with glycosidic enzymes liberates biologically active split products. This process proceeds rapidly and in an uncontrolled fashion when *Aloe barbadensis* gel materials are processed under usual industrial conditions. This process can be better controlled by producing Aloe gel in its native state and then activating it with commercial enzymes. However, the composition of matter of biologically active materials produced by this process and the optimal method of controlling the activation process arebeing further defined.

EXAMPLE 4

Production of An Activity Restoring Contact Hypersensitivity (CHS) to DNFB in Mice Exposed to UVB Radiation by Treatment of *Aloe barbadensis* Polysaccharide with Purified Cellulase Previous studies demonstrated that *Aloe barbadensis* gel in the native state had relatively little biological activity but that it could be activated by treatment with commercial cellulase. This increased the ability of the gel to restore skin immune system activity suppressed by exposure to UVB radiation in vivo. Cellulase treatment also increased the ability of Aloe gel to activate cultured macrophage as measured by chemiluminescence. This increased activity was accompanied by a change in the polysaccharide in Aloe gel from a very high molecular weight form to one resembling that classically described. These effects were suggestive of a mechanism whereby a biologically inactive precursor polysaccharide was cleaved by a glycosidase into biologically active fragments. This supposition was tested by purifying polysaccharide by the method of Gowda et al. and treating it with purified cellulase. After enzyme treatment, polysaccharide and enzyme were precipitated by ethanol leaving buffer and small cleaved products in the supernatant. Oligosaccharide-containing supernatant and polysaccharide-containing precipitate were then chemically analyzed and tested for biological activity.

Figure 5:
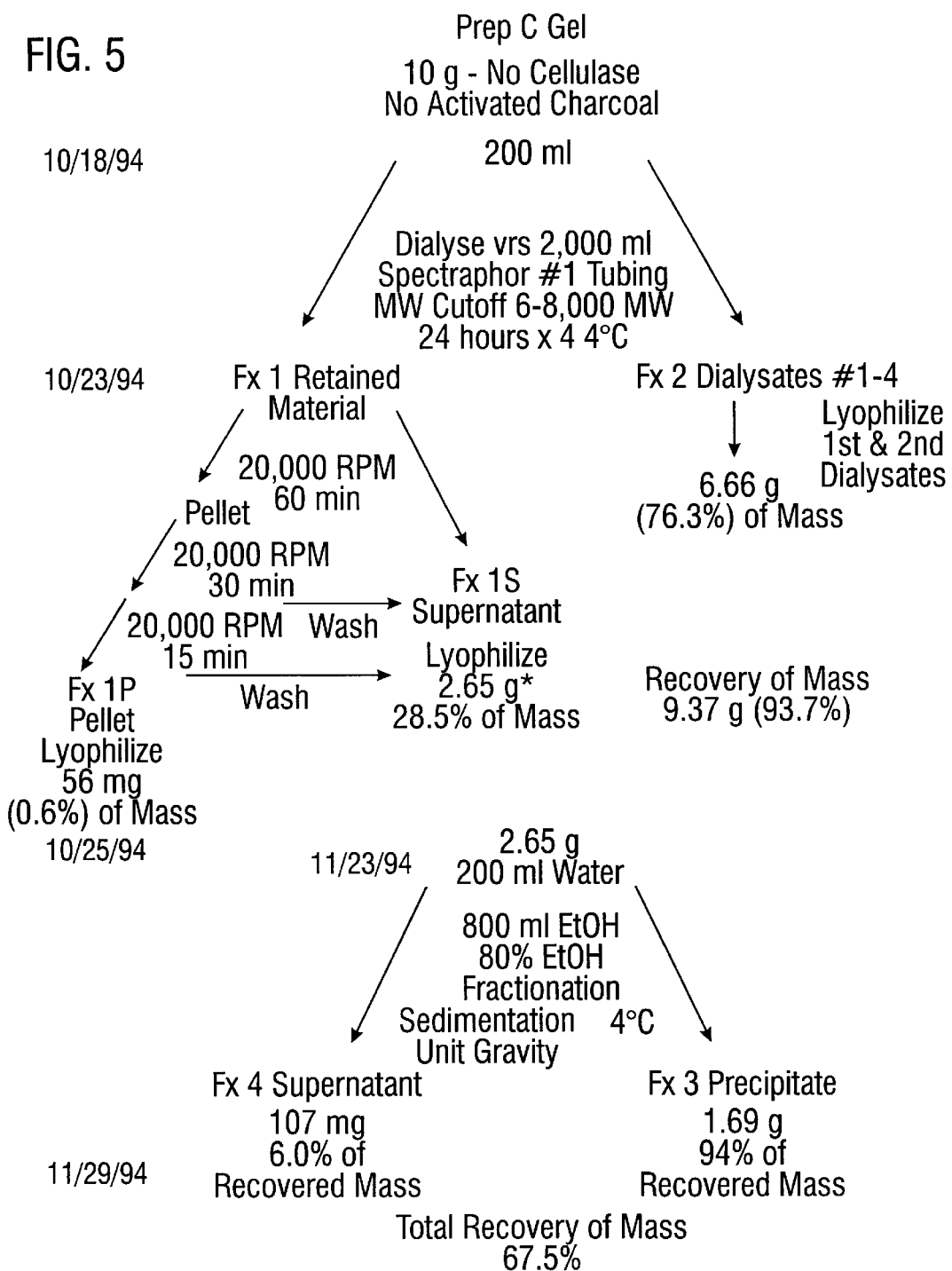
FIG. 5 schematically shows purification of polysaccharide from Prep CJ Process A *Aloe barbadensis* gel.

Polysaccharide Purification. Native polysaccharide was purified by dialysis and ethanol precipitation from Preparations C and D. FIG. 5 illustrates the isolation of native polysaccharide from Prep C. Ten grams of *Aloe barbadensis* gel, produced by ultra-clean process and lyophilized from 1:1 gel without any Pasteurization, filtration, concentration or enzyme treatment (Process A, Aloe) was reconstituted with 200 ml reverse osmosis purified water (RO water) by homogenization. This was exhaustively dialyzed against 5 volumes of RO water at 4° C. Dialysis was monitored by conductivity and after the 4th cycle of dialysis, conductivity of dialysate was less than 100 µSiemens. This procedure yielded approximately 2.7 grams of highly pseudoplastic retained material. Insoluble fiber was removed from this crude polysaccharide Fraction 1 by centrifugation. Because of the high degree of pseudoplasticity, it was necessary to wash the pellet twice in order to achieve a high degree of recovery of supernatant. The supernatant Fraction 1 was lyophilized and stored at 4° C. until further use. The yield of Fraction 1 crude polysaccharide was 2.65 g (28.5% of mass).

This value must be interpreted with caution because of the high water content of the hygroscopic material.

The second step in polysaccharide purification was precipitation with alcohol (FIG. 5, lower portion). This step partitioned 94% of the 80% ethanol-precipitated recovered mass in the purified polysaccharide Fraction 3. The supernatant (Fraction 4) consisted of materials (sterols, anthraquinone, aglycones, chromone esters, etc.) too polar to cross the relatively hydrophilic cellulose membrane and saccharides of too small a size to be alcohol precipitable. It should be noted that Process A, *Aloe barbadensis* gel is low in anthraquinones and chromones by virtue of meticulous filleting. Furthermore, because rind contamination is low and the gel has been held at low temperature prior to arrival at the processing plant, cleavage fragments from endogenous glycosidases promoting polysaccharide breakdown is minimal. Therefore, Process A Aloe gel has a very low proportion of Fraction 4 material versus Fraction 3 polysaccharide. The yield of Fraction 4 was 1.1% and the yield of Fraction 3 polysaccharide was 16.9%.

Polysaccharide was also purified from 10 grams of Process A gel from Prep. D. There were three minor differences in the protocol followed for Prep C polysaccharide isolation. Because the amount of fiber was so low in the previous isolation (56 mg, 0.6%), the centrifugation step after dialysis was omitted. Also, ten percent of the Fraction 1 material was reserved for other analyses. Lastly, after ethanol fractionation, the precipitate was separated by centrifugation rather than sedimentation. The all-over yield of polysaccharide was similar (14.2 versus 16.9%, correcting for reserved material) as was the amount of Fraction 4 material (1.8% versus 1.1%).

Basic chemical analyses of these types of polysaccharide reveals the following. The total hexose content of Fraction 3 polysaccharide was 73±6% (mean±S.E.M. of 10 determinations). Of the total hexose, 4.4% was reducing sugar for a total hexose to reducing sugar ratio of 22.7:1.

The sugar composition of the polysaccharides was determined by hydrolysis and HPLC. Two to three milligrams of polysaccharide powder was placed into a 5 ml Pierce hydrolysis tube and 1 to 2 ml of 6N redistilled, constant boiling HCI was added. The tubes were chilled and purged of air by several cycles of evacuation and replenishment with nitrogen followed by final evacuation. The polysaccharides were then hydrolysed by heating to 120° C. for 30 minutes. After cooling, the samples were neutralized with 5N NaOH and the total hexose content determined by Dubois assay. The samples are then adjusted to a hexose content of 20 µg/ml and the substituent monosaccharides are measured on a Dionex bonded amino column at basic pH. Sugars are quantitated with a pulsed amphoteric detector. These analyses indicate that Fraction 3 polysaccharide has the following sugar composition (mean±S.E.M., 15 determinations): glucose, 7±1%; mannose, 85±1%, galactose, 4±1%. There are trace amounts of glucosamine and galactosamine detected.

Purification of Cellulase. Crude *T. reesei* concentrated culture supernatants (lot #ZPED) were obtained from Valley Research Inc. (South Bend, Ind.). Cellulase enzymatic activity was measured by the method of Fernley (1993 *Biochem. J.*, 87, 90–95) using Cellulose Azure (Sigma). Absolute ethanol was added dropwise to 130 ml of concentrate (solids content 39.5 g) at ambient temperature until a green-brown syrupy gum formed at 50% alcohol concentration. The supernatant was removed from the gum (dried mass 11.0 g). Further ethanol was added until a light tan copious precipitate formed at 80% ethanol concentration. The precipitate was removed by centrifugation at 10,000×G for 10 minutes at 4° C. The precipitate was dissolved in RO water and lyophilized (mass, 5.8 grams). Although some cellulase activity was present in the 50% ethanol fraction and in the 80% ethanol supernatant, the highest specific activity was present in the 50–80% alcohol fraction.

Partially purified cellulase (2 grams) was dissolved in 4 ml of RO water and clarified by centrifugation at 13,000×G for 10 minutes at 4° C. The pellet, devoid of enzyme activity, was discarded. The solubilized supernatant was applied to a 2.5×95 cm column of Biogel P-200 gel. The size-exclusion, gel-filtration column was eluted with a 0.0125% sodium azide buffer at a flow rate of 18 ml per hour and 5 ml fractions were collected.

Protein in eluates was crudely measure by optical density at 280 nm assuming an extinction coefficient of 4 ODU/mg. Salts were assessed by conductivity. Protein eluted as a major peak at a Ve of 380 nm (Vo, 117 ml; Vt, 469 ml), consistent with a molecular weight of ~40,000. There was a smaller peak of $OD_{280\ nm}$-absorbing material at 420 ml. Five pools were made (average volume 44 ml) of fractions throughout this region and protein content was determined by binding of Coumassie Blue dye using a bovine serum albumin standard. Protein content of the 5 pools was 400 mg. Aliquots (3 and 15 µg protein content) of the pools were incubated with 5 mg amounts of Cellulose Azure dye at 45° C. for 10 minutes. Maximal specific activity (19.9 $ODU_{550\ nm}$Units/mg/min) was observed to correspond with the major protein peak. The pools were lyophilized and stored dessicated at ×20° C.

Effect of Treatment With Purified Cellulase Upon the Physical Properties of Native Aloe Polysaccharide. Two studies were conducted. The first was with Prep C native polysaccharide and the second was with Prep D native polysaccharide. Different amounts of enzyme were incubated at ambient temperature with a constant amount of the highly pseudoplastic polysaccharide and the change in viscosity with time was measured. The reaction was stopped by precipitating enzyme and polysaccharide with 80% ethanol. Then the chemical composition of the supernatant was determined and the molecular weight of the precipitated polysaccharide was examined by gel filtration on Sepharose 4B.

Figure 6:
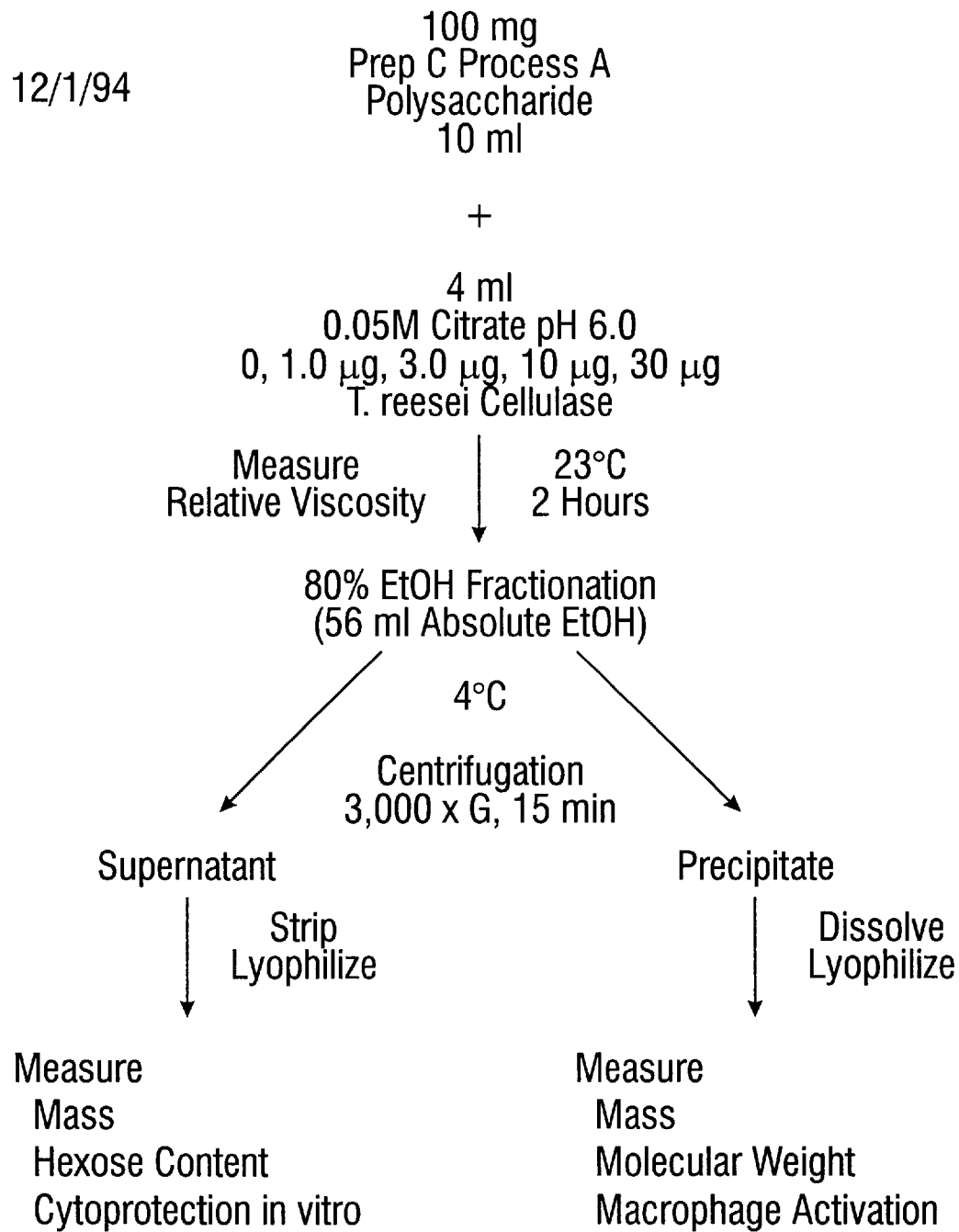
FIG. 6. schematically shows the protocol for treatment of Prep C Process A native polysaccharide with *T. reesei* cellulase.

In the case of Prep C polysaccharide (FIG. 6), 100 mg of polysaccharide (10 mg/ml, 10 ml) was mixed with 4 ml of 0.05M citrate pH 6.0 containing either no cellulase or varying amounts (1, 3, 10, or 30 µg protein content) of cellulase. At various times (5 to 120 minutes) after mixing, relative viscosity was determined as the rate of flow of a 10 ml portion through a restricted (0.5 mm) orifice (flow between the 12 ml and 2 ml markers on Corning "10 ml" pipettes). All values were normalized to water and naive polysaccharide flow times for that individual pipette by the following formula:

$$\text{Relative Viscosity} = \frac{\text{Time of Flow Experimental} - \text{Time of Flow of Water}}{\text{Time of Flow, O Time} - \text{Time of Flow of Water}} \times 100$$

Figure 7:
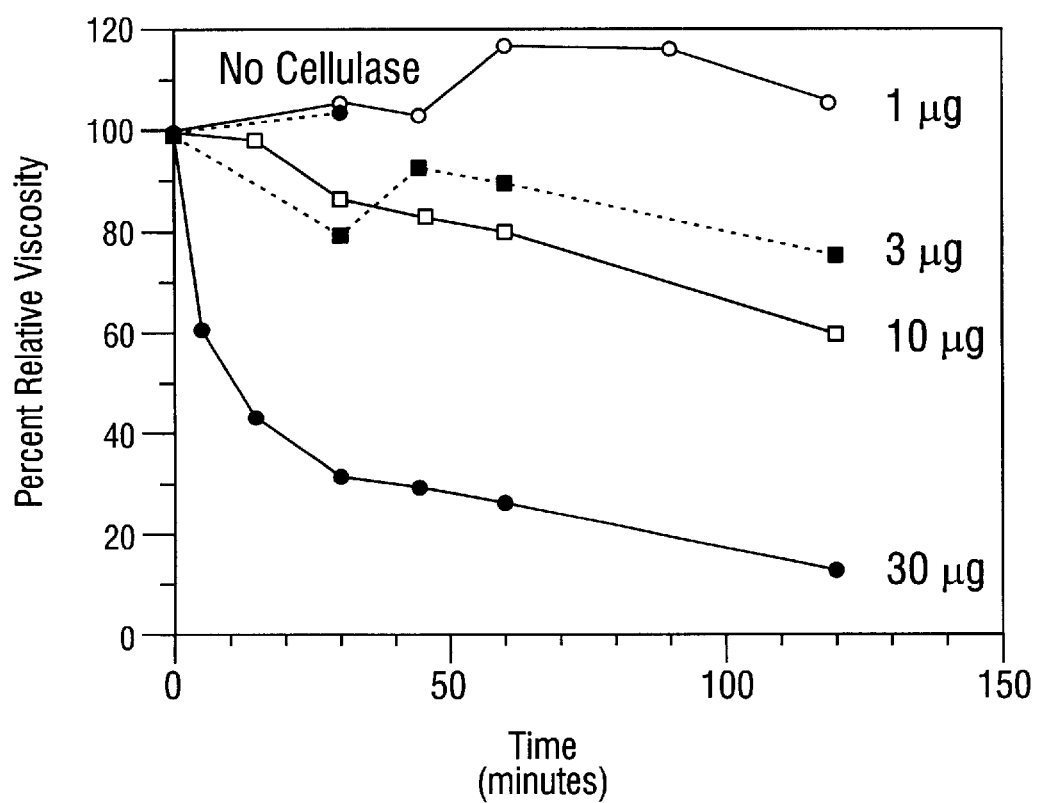
FIG. 7 shows the effect of time and cellulase concentration upon relative viscosity of Prep C Process A native polysaccharide. Purified polysaccharide (100 mg, 10 mg/ml) was mixed with 4 ml of 0.05M citrate buffer pH 6.0 containing varying amount of cellulase (no cellulase □, 1 μg cellulase ♦, 3 μg cellulase, ■, 10 μg cellulase o- or 30 μg cellulase, ●). The samples were incubated at ambient temperature and relative viscosity was measured at periodic intervals over the next two hours by flow through a pipette. All values were normalized to flow rate of water through that individual pipette and flow at o Time by the formula.
Figure 8A:
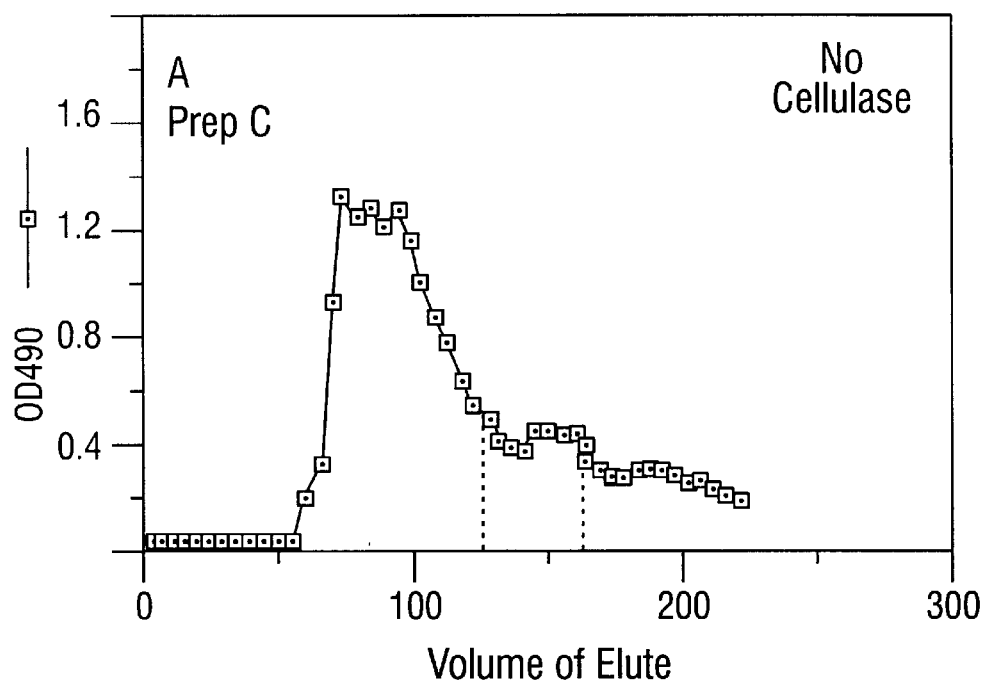
Figure 8B:
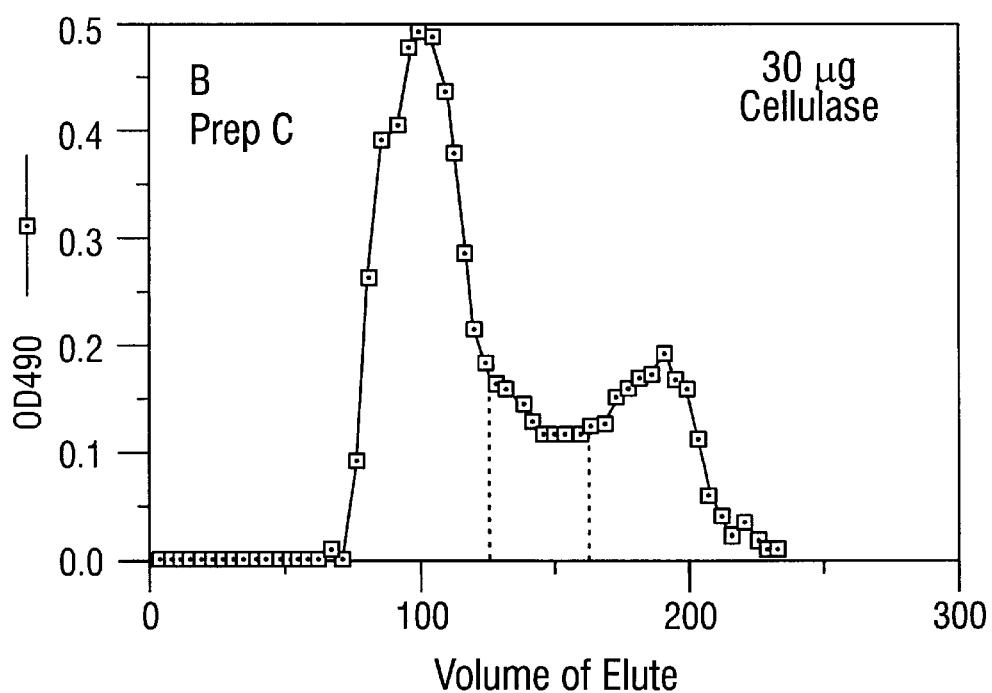
Figure 8C:
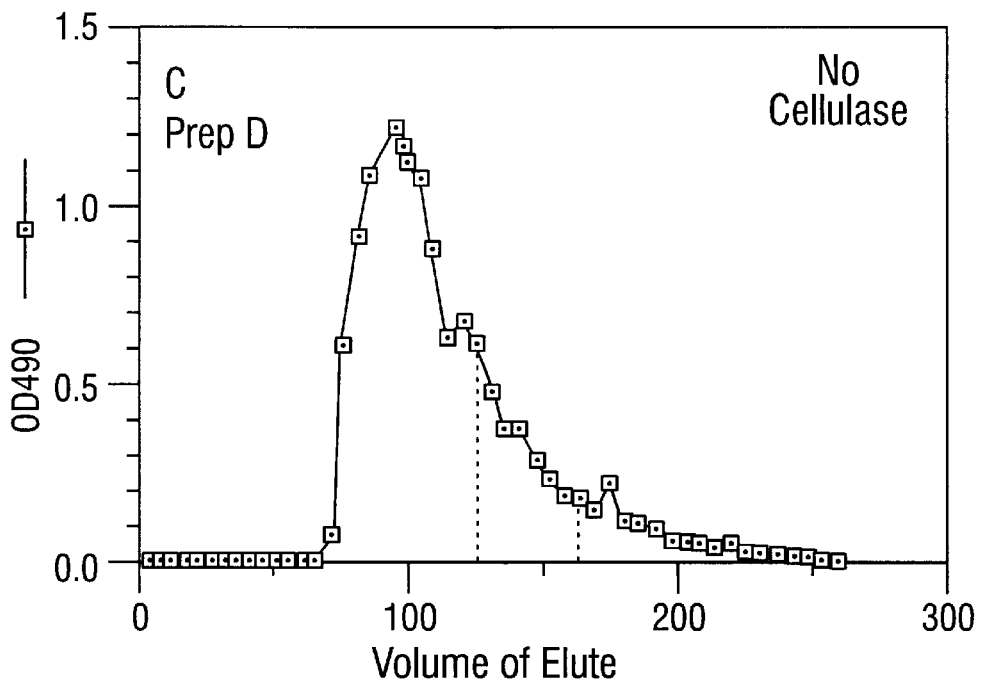
Figure 8D:
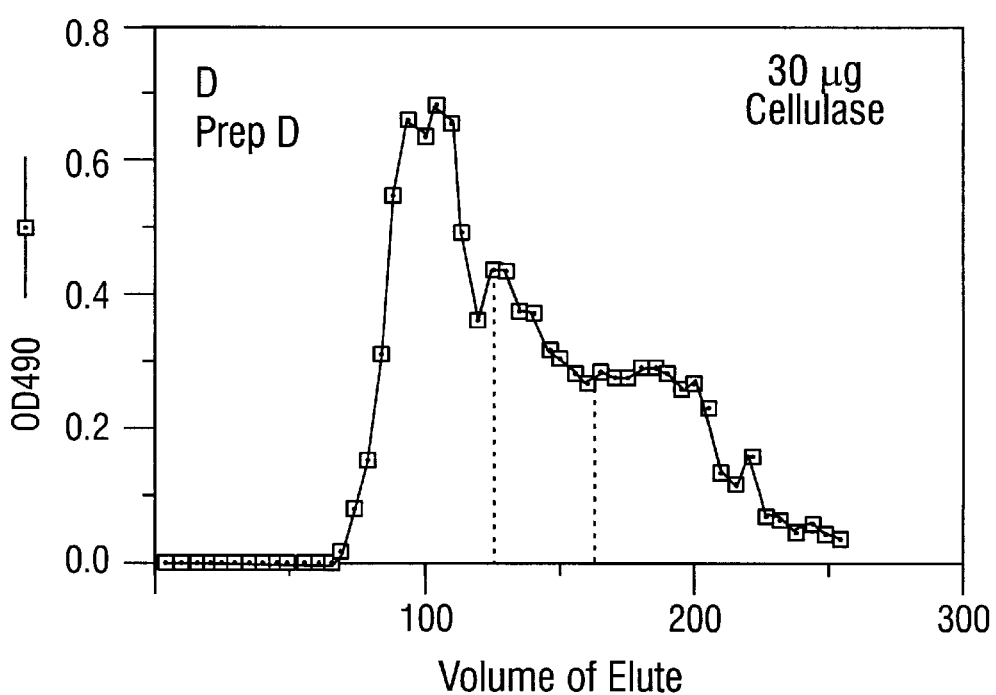

FIG. 7 illustrates the effect of cellulase treatment upon the relative viscosity of Prep C polysaccharide. No effect was observed in the absence of cellulase or at very low (1 µg cellulase per 100 mg polysaccharide) doses. Intermediate doses of cellulase (3 to 10 µg cellulase per 100 mg polysaccharide) caused a 20 to 40% decrease in relative polysaccharide viscosity over a 2 hour time. At the highest dose of cellulase employed (30 µg cellulase per 100 mg polysaccharide) there was a rapid (within 20 minutes) and precipitous fall in relative viscosity. This then leveled off, yielding a gel that still had some pseudoplasticity. Table 5 summarizes the effects of purified cellulase upon relative viscosity of purified Prep C polysaccharide after 2 hours of incubation.

TABLE 5

Treatment of Purified ARF'94J Polysaccharide with Purified Cellulase[a]

| Concentration of Cellulase[b] | Relative Viscosity[c] | 80% Ethanol Supernatant | |
|---|---|---|---|
| | | Mass[d] | Total Hexose[e] |
| No Cellulase | 104% | 58 mg | 0.23 mg |
| 1 µg | 106% | 70 mg | 0.47 mg |
| 3 µg | 76% | 74 mg | 0.47 mg |
| 10 µg | 60% | 77 mg | 1.22 mg |
| 30 µg | 13% | 83 mg | 3.50 mg |

[a]100 mg of ARF'94J Process A, Fraction 3 polysaccharide (7.1 mg/ml, 0.01 M Citrate, pH 6.0) treated for 2 hours at ambient temperature with various amounts of Cellulase TR. After the incubation, cellulase and polysaccharide were precipitated with 80% cold ethanol. The pellet was redissolved after centrifugation and lyophilized. The supernatant was stripped and lyophilized.
[b]Protein content by Coomassie Blue Dye Binding, BSA standard.
[c]Normalized versus viscosity at 0 Time versus water. values are taken after two hours of incubation at ambient temperature. Mean 0 Time flow rate, 86.7 ± 9.1 seconds per 10 ml (mean ± standard error of mean); water, 4.1 ± 0.1 seconds.
[d]Citrate buffer contribution to mass, 60 mg.
[e]Phenol sulfuric acid test (Dubois method).

A very similar study was performed using polysaccharide isolated from Prep D. For the sake of simplicity, only two cellulase concentrations (3 µg cellulase per 100 mg polysaccharide and 30 µg cellulase per 100 mg polysaccharide) were employed. The study was also performed on a somewhat larger scale (400 mg of polysaccharide rather than 100 mg). In each case, 47.5 ml of polysaccharide solution (8.42 mg/ml, total 400 mg) was mixed with 5 ml of 0.05M citrate, pH 6.0 containing either no cellulase, 12 µg (protein content) cellulase or 120 µg (protein content) cellulase. This yielded solutions of 52.5 ml volume with either no cellulase per 100 mg polysaccharide, 3 µg cellulase per 100 mg polysaccharide or 30 µg cellulase per 100 mg polysaccharide. Relative viscosity was measured at 0 Time (before addition of citrate buffer containing cellulase), 15 minutes, 30 minutes, 1 hour and 2 hours. In all cases, relative viscosity was normalized to the values for water for that pipette and to the 0 Time control using the formula above. This controls for pipette to pipette variability in orifice area. The time/cellulase concentration/relative viscosity profiles are essentially identical to those obtained at the 3 µg cellulase per 100 mg polysaccharide and 30 µg cellulase per 100 mg polysaccharide concentrations in the previous study. Table 6 summarizes the relative viscosity values after 2 hours of incubation at ambient temperature. Comparison with Table 5 reveals that despite the somewhat different scale of the two studies, the 2 hour reductions in viscosity yielded consistent values: 0 cellulase, 93±10% relative viscosity; 3 µg cellulase per 100 mg polysaccharide, 66±10% relative viscosity and 30 µg cellulase per 100 mg polysaccharide, 11±2% relative viscosity (all values mean±range). After 2 hours of cellulase treatment this experiment was also terminated by precipitation of polysaccharide with ethanol.

TABLE 6

Treatment of Purified Prep D Polysaccharide with Purified Cellulase[a]

| Concentration of Cellulase[b] | Relative Viscosity[c] | 80% Ethanol Mass[d] | Supernatant Total Hexose[e] (% Hexose) | Total Hexose: Reducing Sugar[f] |
|---|---|---|---|---|
| No Cellulase | 83% | 109 mg | 0.09 mg (0.83%) | 1.78:1 |
| 3 µg Per 100 mg | 56% | 107 mg | 1.60 mg (1.47%) | 2.13:1 |
| 30 µg Per 100 mg | 9% | 88 mg | 11.6 mg (13.2%) | 10.3:1 |

[a] 300 mg of ARF'94K Process A, Fraction 3 polysaccharide (6.0 mg/ml, 0.005 M Citrate, pH 6.0) treated for 2 hours at ambient temperature with various amounts of Cellulase TR. After the incubation, cellulase and polysaccharide were precipitated with 80% cold ethanol. The supernatant was then stripped and lyophilized.
[b] Protein content by Coomassie Blye Dye Binding (Bradford method), BSA standard.
[c] Normalized versus viscosity at 0 Time versus water. Mean 0 Time flow rate, 86.7 ± 9.1 seconds per 10 ml (mean ± standard error of mean); water, 4.1 ± 0.1 seconds.
[d] Citrate buffer contribution to mass, 75 mg.
[e] Phenol sulfuric acid test (Dubois method).
[f] Neocuproine test (Thoma method).

The effect of this cellulase cleavage upon the distribution of molecular weights of the polysaccharide was assessed by size-exclusion gel-filtration. FIG. 8 illustrates the profiles for Prep C polysaccharide treated by incubation alone (Panel A) and treated with the highest dose of cellulase (Panel B, 30 µg cellulase per 100 mg polgysaccharide) and for Prep D polysaccharide treated by incubation alone (Panel C) and treated with the highest dose of cellulase (Panel D, 30 µg cellulase per 100 mg polysaccharide). In the absence of cellulase treatment most of the polysaccharide (FIG. 8, Panels A and C) was in the highest molecular weight form (69.4±7.0% mean±the range of the two determinations). Relatively little polysaccharide was in the molecular weight range classically described for "Acemannan" (14.5±5.5%, mean±the range of the two determinations). It should be recalled (Example 1) that when crude Process A *Aloe barbadensis* gel was treated with commercial "cellulase", even the lowest concentration of "cellulase" utilized completely converted the constituent polysaccharide to the lower molecular weight form. When purified native polysaccharide was treated with the highest concentration of purified cellulase under a protocol that reduces relatively viscosity 89%, the resultant polysaccharide, although shifted in its molecular weight distribution (FIG. 8, Panels B and D) was only partially converted to the lower molecular weight form. High molecular weight polysaccharide was reduced 22% (69.4±7.0% to 53.9±6.0%). Polysaccharide of intermediate molecular weight increased 16% (16.1±1.5% to 18.7±3.5%) and polysaccharide in the lowest molecular weight category increase 88% (14.5±5.5% to 27.3±2.5%). Thus, although treatment of pure polysaccharide with sufficient purified cellulase to drastically reduce pseudoplasticity alters the molecular weight distribution, most of the polysaccharide (53.9±6.0) is still in a relatively high molecular weight form and relatively little (27.3±2.5%) is in the structure A form.

Biological Activity of Polysaccharide Treated with Purified Cellulase. Example 1 indicated that treatment of crude native *Aloe barbadensis* gel with commercial "cellulase" resulted in the generation of several biological activities.

Included in these activities was that which is classically ascribed to Aloe polysaccharide—activation of phagocytic cells such as neutophilic polymorhponuclear leukocytes and macrophages. We hypothesized from those findings that what was occurring was the activation of a biologically inactive form of the polysaccharide—the high molecular native polymer—by cellulase cleavage to a lower molecular weight form. However, this was difficult to test using crude Aloe material and an industrial enzyme that potentially contains many different components. FIG. 9 illustrates testing of this hypothesis using more highly purified materials.

Polysaccharide purified from native, Process A *Aloe barbadensis* gel has little effect upon cultured macrophages. Treatment of this isolated polysaccharide with low doses (1 to 3 µg per 100 mg) of purified cellulase results in the generation of considerable macrophage-activating activity. However, further treatment of polysaccharide with cellulase (10 to 30 µg per 100 mg) not only failed to increase activation but resulted in a progressive loss of macrophage stimulating activity. It is interesting that this same phenomenon—activation of biological effect at low doses of cellulase but inactivation with higher doses of cellulase—was observed in the crude system examined in Example 2. These studies demonstrate that the loss of activity observed with high concentrations of cellulase is not simply due to a complete destruction of polysaccharide since FIG. 8, Panel B demonstrates that the cellulase treatment did not even convert all of the polysaccharide to the "cleaved" form. In conclusion, it appears likely that the phagocyte-activation principle in Aloe does indeed consist of a partially cleaved polysaccharide and that excess action of cellulase will cause a loss of biological activity.

Chemical Analyses of Ethanol Soluble Products of Digestion. In the above studies, after cleavage of polysaccharide with cellulase, both the polysaccharide and the cellulase were precipitated with alcohol. The supernatant was stripped of ethanol and examined for the products of this digestion (Tables 5 and 6). In the absence of cellulase, the ethanol supernatant had a very low (<1%) content of hexose. Almost all of the mass could be accounted for by the citrate buffer (which will remain in the supernatant upon alcohol fractionation).

The fractionation process preparing the polysaccharide involves exhaustive dialysis followed by alcohol precipitation. However, as the polysaccharide was cleaved with cellulase, saccharide of sufficiently low molecular weight so as to be alcohol soluble was produced. There was a very direct relationship between the amount of enzyme employed and the amount of alcohol soluble hexose liberated. The highest ratio of enzyme to polysaccharide substrate yielded a 12.9 (Prep C) to 15 (Prep D) fold increase in alcohol soluble hexose above the no enzyme control.

In the study described in Table 6, the form of this alcohol soluble saccharide was determined by finding the ratio between total hexose and reducing sugar. Monosaccharides have a total hexose to reducing sugar ratio of 1: 1, disaccharides have a ratio of 2:1 and oligosaccharides and polysaccharides have ratios greater than 2:1. The small amount of sugar present in 0 Cellulase controls has a total hexose to reducing sugar ratio consistent with a mixture of monosaccharides and higher sugars. This was confirmed by Dionex HPLC analysis which revealed a significant amount of glucose (65%) and fructose (10%) the free sugars that are predominant among the monosaccharides in *Aloe barbadensis* gel. As digestion proceeded, the ratio of total hexose to reducing sugar rose to a maximum of 10.3:1. This suggests either the production of an oligosaccharide or of a polysaccharide with significant branching. Hydrolysis of these supernatants followed by Dionex HPLC analysis for substituent sugars revealed a glucose:mannose ratio of 1:0.25±0.01 (mean±range of determinations on 3 µg and 30

μg cellulase supernatants). This is almost exactly the opposite (glucose:mannose of 1:6 to 1: 15) one would expect from the hydrolysis of native polysaccharide or structure A. Thus, in addition to cellulase cleaving an ethanol-insoluble structure. A like polysaccharide fragment from the native polysaccharide, there appears to be a second alcohol-soluble fragment liberated with composition of matter unlike structure A.

Biological Activities in Ethanol Supernatants of Cellulase Digests. At least three activities have been ascribed to *Aloe barbadensis* gel: phagocyte stimulation, restoration of the skin immune system after injury by UVB radiation, and enhanced recovery of epithelial cells after physical injury.

The inventors determined if the non-"Acemannan", alcohol-soluble fragment cleaved from native polysaccharide by cellulase possessed any of these biological activities. The alcohol supernatants were tested for the ability to activate cultured macrophages using the same system employed in FIG. 9. There was no significant phagocyte stimulating activity in the supernatants. Thus, macrophage activation appears to be associated with cleavage of native polysaccharide into "Acemannan"-like molecules and is not the property of either native polysaccharide per se or the non-"Acemannan"-like cleavage oligosaccharide.

On the other hand (Table 7) the oligosaccharide fraction was active at very high dose (0.005%) in preventing suppression of the skin immune system by Ultraviolet β radiation. This effect was not present in supernatants of polysaccharide not treated with cellulase and the activity was destroyed by exposure to high cellulase.

U.S. Patents
Baron, U.S. Pat. No. 4,788,007, Nov. 29, 1988 Class 252 Subclass 589
Coats, U.S. Pat. No. 4,178,372
Coats, U.S. Pat. No. 5,356,811, Oct. 18, 1994
Cobble, U.S. Pat. No. 3,892,853
Farkas, U.S. Pat. No. 3,103,466, Sep. 10, 1963)
Goldstein, U.S. Pat. No. 4,500,510
Gruber, U.S. Pat. No. 4,593,046
Kydiskis, U.S. Pat. No. 4,670,265
Lindauer et al., U.S. Pat. No. 4,627,934
Maret, U.S. Pat. No. 3,878,197
McAnalley, U.S. Pat. No. 4,851,25, Jul. 25, 1989
McAnalley, U.S. Pat. No. 4,959,214, Sep. 25, 1990
McAnalley, U.S. Pat. No. 4,966,892
McAnalley, U.S. Pat. No. 4,735,935, Apr. 5, 1988, Class 514 Subclass 53.
Rosenthal, U.S. Pat. No. 4,585,656.

Publications in the Scientific Literature
Andersen et al., "Ultraviolet B Dose-Dependent Inflammation in Humans: a Reflectance Spectroscopic and Laser Doppler Flowmetric Study Using Topical Pharmacologic Antagonists on Irradiated Skin", *Photodermatol., Photoimmunol. & Photomed.* 9:17–23 (1992)
Bergstresser, "Sensitization and Elicitation of Inflammation in Contact Dermatitis", *Immunology Series,* 46:219–245 (1989)
Davis et al., "Processed *Aloe vera* administered topically inhibits inflammation", *J. Amer. Podiatric Med Assoc.* 79:395–397 (1987))
Fernley, *J. Biochem.,* 87, 90–95, (1993)

TABLE 7

Treatment of Purified Prep D Polysaccharide with Purified Cellulase[a]
Restoration of CHS Response to DNFB Subsequent to 2 kJ/m$^2$ UVB Radiation Exposure[b]

| Concentration of Ethanol Supernatant of Digest | | Ethanol Supernatant of Digest Concentration of Cellulase per 100 mg Polysaccharide | | |
|---|---|---|---|---|
| | | None | 3 μg | 30 μg |
| 0.5% | Ear Swelling[c] | 7.7 ± 0.3 | 5.6 ± 0.1 | 7.5 ± 1.3 |
| | % Restoration of CHS[d] | 2.8 ± 4.0% | −22.0 ± 3.1% | 4.2 ± 7.6% |
| | n | 5 | 5 | 5 |
| 0.05% | Ear Swelling | 95 ± 1.1 | 8.4 ± 0.4[e] | 8.0 ± 0.5 |
| | % Restoration of CHS | 31.9 ± 14.7% | 16.7 ± 6.0% | 11.1 ± 7.3% |
| | n | 4 | 5 | 5 |
| 0.005% | Ear Swelling | 7.9 ± 0.8 | 13.0 ± 1.1[e] | 7.2 ± 0.6 |
| | % Restoration of CHS | 9.7 ± 11.1% | 80.6 ± 15.3% | 0.0 ± 8.4% |
| | n | 5 | 4 | 5 |

[a]400 mg of Prep D Process A, Fraction 3 polysaccharide (6.0 mg/ml, 0.005 M Citrate, pH 6.0) treated for 2 hours at ambient temperature with various amounts of Cellulase TR. After the incubation, cellulase and polysaccharide were precipitated with 80% cold ethanol. The supernatant was then stripped and lyphilized.
[b]Mice were exposed to UVB radiation and the area of irradiated skin was immediately treated with ethanol supernates of cellulase digests reconstituted in RO water. Four days later mice were sensitized on the irradiated area with DFNB. Seven days were then allowed for the immune response to develop. Mice were then challenged by application of DNFB to the ears. The next day, immunological reactivity was measured by quantitating ear swelling.
[c]Measured as mm × 10$^{-2}$, mean ± S.E.M. Controls (5 animals in each group) consisted of: Negative Controls (no sensitization, 2.9 ± 0.4), Positive Controls (no UVB radiation, 14.4 ± 1.0), UVB Suppressed (UVB radiation, Sensitized, 7.2 ± 0.7), Citrate Control (Sensitization, Citreate buffer, no UVB, 14.7 ± 0.8), Citrate Treatment Control (Sensitization, UVB radiation, Citrate Buffer treatment, 5.3 ± 0.8).
[d]Values normalized to UVB Suppressed Controls and Positive Controls by the formula [(Treatment swelling − Suppressed Control swelling)/Positive Control swelling] × 100.
[e]Significant by T test versus citrate control; 3 μg cellulase digests; 0.05%, p = 0.02, 0.005%, p = 0.015

REFERENCES

The following references, to the extent that they provide exemplary procedural or other details supplementary to those set forth herein, are specifically incorporated herein by reference.

Gowda et al., "Structural studies of polysaccharides from *Aloe vera.*" *Carb. Res.* 72:201–205, 1979.
Gowda. "Structural studies of polysaccharides from *Aloe saponaria* and *Aloe vanbalenii.*" *Carbohydrate Research* 83:402–405, 1980.

Hadiabi, et al. "Structural studies of the glucomannan from *Aloe vahombe*." *Carbohydrate Research* 116: 166–170, 1983.

Kripke. "Effects of UV Irradiation on Tumor Immunity", *J. Natl. Canc. Inst. U.S.* pp 1392–1396 (1990)

Lee, *J. Invest. Dermatol.* 609–610 (1991).

Mandal et al. "Structure of the glucomannan isolated from the leaves of *Aloe barbadensis* Miller." *Carb. Res.* 87:249–256, 1980.

Mandal et al. "Characterization of polysaccharides of *Aloe barbadensis* Miller: Part III—Structure of an acidic oligosaccharide." *Ind. J. Chem.* 22B:890–893.

Mandal et al. "Structure of the D-galactan isolated from *Aloe barbadensis* Miller." Carb. Res. 86:247–257, 1980.

Paulsen, et al. "Structural studies of the polysaccharides from *Aloe plicatilis* Miller." *Carb. Res.* 60:345–351, 1978.

Pelley et al. "Aloe polysaccharides and their measurement." *Inside Aloe*, Feb. 1996, Supplement, p 1–4.

Radjabi-Nassab, et al. "Further studies of the glucomannan from *Aloe vahombe* (liliaceae). II. Partial hydrolyses and NMR $^{13}$C studies." *Biochimie* 66:563–567, 1984.

Reeve et al., "The Protective Effect of Indomethacin on Photocarcinogenesis in Hairless Mice", *Cancer Letters*, 95:213–(1995)

Reeve et al., Differential Protection by Two Sunscreens from UV Irradiation-Induced Immunosuppression, *J. Invest. Dermatol.* 97:624–628 (1991)

Roboz et al. "A Mucilage from *Aloe Vera.*" *J. Am. Chem. Soc.* 70:3248–3249, 1948.

Solar, et al. *Arch. Inst. Pasteur Madagascar.* 47:1–31, 1979.

Vermeer et al., "Effects of Ultraviolet B Light on Cutaneous Immune Responses of Humans with Deeply Pigmented Skin", J. Invest. Dermatol., 97:729–734 (1991).

Von Praag et al., "Effect of Topical Sunscreens of the UV-Irradiation-Induced Suppression of the Alloactivating Capacity in Human Skin In Vivo", J. Invest. Dermatol., 97:629–633 (1991).

Wolf et al., "Analysis of the Protective Effects of Different Sunscreens on Ultraviolet Irradiation-Induced Local and Systemic Suppression of Contact Hypersensitivity and Inflammatory Responses in Mice", J. Invest. Dermatol. 100:254–259.

Womble et al. "Enhancement of allo-responsiveness of human lymphocytes by Acemannan (Carrisyn™)." *Int. J. Immunopharmac.* 10:967–974, 1988.

Yagi, et al. "Aloe mannan, polysaccharide, from *Aloe arborescens* var. *natalensis*

What is claimed is:

1. A purified oligosaccharide having a molecular weight of 1,000–5,000 daltons, said oligosaccharide being separated from Aloe and is able to inhibit loss of skin immunocompetency induced by ultraviolet irradiation, wherein said olicosaccharide is about 75% glucose, about 25% mannose and with trace galactose.

2. The oligosaccharide of claim 1 defined further as having a total hexose to reducing sugar ratio of about 10:1.

3. The oligosaccharide of claim 1 defined further as being obtained by cellulase cleavage of a precursor block polysaccharide of Aloe.

4. A therapeutic composition for alleviation of UV-induced skin immune system damage comprising the oligosaccharide of claim 1 and a pharmaceutically acceptable excipient.

5. A method for obtaining the immunoprotective oligosaccharide of claim 1, the method comprising treating an Aloe extract with cellulase at a concentration of less than about 2 grams per 215 liters and separating the oligosaccharide from cellulase and polysaccharide by dialysis or precipitation with lower aliphatic alcohol.

6. A method for inhibiting immunosuppression induced by ultraviolet irradiation, the method comprising topically administering the oligosaccharide of claim 1 to an animal subjected to ultraviolet irradiation.

* * * * *

UNITED STATES PATENT AND TRADEMARK OFFICE
CERTIFICATE OF CORRECTION

PATENT NO. : 5,824,659

DATED : October 20, 1998

INVENTOR(S) : Strickland, Pelley and Kripke

It is certified that error appears in the above-identified patent and that said Letters Patent is hereby corrected as shown below:

In claim 1, column 32, line 16, delete "olicosaccharide" replace --oligosaccharide--.

Signed and Sealed this

Twelfth Day of January, 1999

Attest:

Attesting Officer

*Acting Commissioner of Patents and Trademarks*